US008323320B2

(12) United States Patent
Lowry et al.

(10) Patent No.: US 8,323,320 B2
(45) Date of Patent: Dec. 4, 2012

(54) TRANSCORPOREAL SPINAL DECOMPRESSION AND REPAIR SYSTEM AND RELATED METHOD

(75) Inventors: David Lowry, Holland, MI (US); Desmond O'Farrell, Grand Rapids, MI (US); Scott Tuinstra, Holland, MI (US); Roger Veldman, Hudsonville, MI (US)

(73) Assignee: TransCorp, Inc., Ada, MI (US)

( * ) Notice: Subject to any disclaimer, the term of this patent is extended or adjusted under 35 U.S.C. 154(b) by 1039 days.

(21) Appl. No.: 12/210,089

(22) Filed: Sep. 12, 2008

(65) Prior Publication Data
US 2009/0076555 A1   Mar. 19, 2009

Related U.S. Application Data

(60) Provisional application No. 60/972,192, filed on Sep. 13, 2007.

(51) Int. Cl.
*A61B 17/80* (2006.01)
(52) U.S. Cl. ...................................... 606/280
(58) Field of Classification Search ............... 606/86 A, 606/86 B, 86 R, 96, 97, 279–281
See application file for complete search history.

(56) References Cited

U.S. PATENT DOCUMENTS

| | | |
|---|---|---|
| 3,741,205 A | 6/1973 | Markolf et al. |
| 5,059,194 A | 10/1991 | Michelson |
| 5,246,458 A | 9/1993 | Graham |
| 5,306,275 A | 4/1994 | Bryan |
| 5,423,826 A | 6/1995 | Coates et al. |
| 5,486,180 A | 1/1996 | Dietz et al. |
| 5,489,307 A | 2/1996 | Kuslich et al. |
| 5,505,732 A | 4/1996 | Michelson |
| 5,645,599 A | 7/1997 | Samani |
| 5,722,977 A | 3/1998 | Wilhelmy |

(Continued)

FOREIGN PATENT DOCUMENTS
DE   4434384 A1   3/1996
(Continued)

OTHER PUBLICATIONS

Lowry et al.; U.S. Appl. No. 11/855,124 entitled "Implantable bone plate system and related method for spinal repair," filed Sep. 13, 2007.

(Continued)

*Primary Examiner* — Nicholas Woodall
(74) *Attorney, Agent, or Firm* — Shay Glenn, LLP

(57) ABSTRACT

A system and method are provided for making an access channel through a vertebral body to access a site of neural compression, decompressing it, and repairing the channel to restore vertebral integrity. System elements include an implantable vertebral plate, a guidance device for orienting bone cutting tools and controlling the path of a cutting tool, a bone cutting tool to make a channel in the vertebral body, a tool for opening or partially-resecting the posterior longitudinal ligament of the spine, a tool for retrieving a herniated disc, an implantable device with osteogenic material to fill the access channel, and a retention device that lockably-engages the bone plate to retain it in position after insertion. System elements may be included in a surgery to decompress an individual nerve root, the spinal cord, or the cauda equina when compressed, for example, by any of a herniated disc, an osteophyte, a thickened ligament arising from degenerative changes within the spine, a hematoma, or a tumor.

15 Claims, 26 Drawing Sheets

U.S. PATENT DOCUMENTS

| | | | |
|---|---|---|---|
| 5,741,253 | A | 4/1998 | Michelson |
| 5,766,253 | A | 6/1998 | Brosnahan, III |
| 5,772,661 | A | 6/1998 | Michelson |
| 5,795,291 | A | 8/1998 | Koros |
| 5,797,909 | A | 8/1998 | Michelson |
| 5,800,433 | A | 9/1998 | Benzel et al. |
| 5,851,207 | A | 12/1998 | Cesarone |
| 5,893,890 | A | 4/1999 | Pisharodi |
| 5,984,922 | A | 11/1999 | McKay |
| 6,056,749 | A | 5/2000 | Kuslich |
| 6,066,142 | A | 5/2000 | Serbousek |
| 6,080,155 | A | 6/2000 | Michelson |
| 6,096,038 | A | 8/2000 | Michelson |
| 6,102,950 | A | 8/2000 | Vaccaro |
| 6,159,214 | A | 12/2000 | Michelson |
| 6,193,721 | B1 | 2/2001 | Michelson |
| 6,207,498 | B1 | 3/2001 | Chen et al. |
| 6,224,599 | B1 | 5/2001 | Baynham et al. |
| 6,224,607 | B1 | 5/2001 | Michelson |
| 6,231,610 | B1 | 5/2001 | Geisler |
| 6,241,733 | B1 | 6/2001 | Nicholson et al. |
| 6,258,094 | B1 | 7/2001 | Nicholson et al. |
| 6,261,293 | B1 | 7/2001 | Nicholson et al. |
| 6,287,313 | B1 | 9/2001 | Sasso |
| 6,315,795 | B1 | 11/2001 | Scarborough et al. |
| 6,332,887 | B1 | 12/2001 | Knox et al. |
| 6,342,056 | B1 | 1/2002 | Mac-Thiong et al. |
| 6,348,058 | B1 | 2/2002 | Melkent et al. |
| 6,371,986 | B1 | 4/2002 | Bagby |
| 6,383,186 | B1 | 5/2002 | Michelson |
| 6,385,475 | B1 | 5/2002 | Cinquin et al. |
| 6,413,259 | B1 | 7/2002 | Lyons et al. |
| 6,440,139 | B2 | 8/2002 | Michelson |
| 6,447,544 | B1 | 9/2002 | Michelson |
| 6,461,359 | B1 | 10/2002 | Tribus et al. |
| 6,517,544 | B1 | 2/2003 | Michelson |
| 6,558,390 | B2 | 5/2003 | Cragg |
| 6,562,046 | B2 | 5/2003 | Sasso |
| 6,562,074 | B2 | 5/2003 | Gerbec et al. |
| 6,572,619 | B2 | 6/2003 | Santilli |
| 6,579,290 | B1 | 6/2003 | Hardcastle et al. |
| 6,599,292 | B1 | 7/2003 | Ray |
| 6,607,530 | B1 | 8/2003 | Carl et al. |
| 6,648,917 | B2 | 11/2003 | Gerbec et al. |
| 6,663,637 | B2 | 12/2003 | Dixon et al. |
| 6,709,438 | B2 | 3/2004 | Dixon et al. |
| 6,740,087 | B2 | 5/2004 | Knox |
| 6,770,074 | B2 | 8/2004 | Michelson |
| 6,837,905 | B1 | 1/2005 | Lieberman |
| 6,859,661 | B2 | 2/2005 | Tuke |
| 6,923,811 | B1 | 8/2005 | Carl et al. |
| 7,014,633 | B2 | 3/2006 | Cragg |
| 7,033,362 | B2 | 4/2006 | McGahan et al. |
| 7,081,119 | B2 | 7/2006 | Stihl |
| 7,083,623 | B2 | 8/2006 | Michelson |
| 7,153,304 | B2 | 12/2006 | Robie et al. |
| 7,163,542 | B2 | 1/2007 | Ryan |
| 7,179,225 | B2 | 2/2007 | Shluzas et al. |
| 7,207,991 | B2 | 4/2007 | Michelson |
| 7,303,565 | B2 | 12/2007 | Buttermann et al. |
| 7,527,641 | B2 | 5/2009 | Suh |
| 7,637,927 | B2 * | 12/2009 | Hyde, Jr. ............... 606/279 |
| 7,837,735 | B2 | 11/2010 | Malone |
| 2001/0047172 | A1 | 11/2001 | Foley et al. |
| 2003/0055427 | A1 | 3/2003 | Graf |
| 2003/0060825 | A1 | 3/2003 | Alfaro et al. |
| 2003/0060828 | A1 | 3/2003 | Michelson |
| 2003/0149341 | A1 | 8/2003 | Clifton |
| 2003/0149434 | A1 | 8/2003 | Paul |
| 2003/0187441 | A1 | 10/2003 | Bolger et al. |
| 2003/0236526 | A1 | 12/2003 | Van Hoeck et al. |
| 2003/0236528 | A1 | 12/2003 | Thramann |
| 2004/0006343 | A1 | 1/2004 | Sevrain |
| 2004/0097925 | A1 | 5/2004 | Boehm et al. |
| 2004/0106924 | A1 | 6/2004 | Ralph et al. |
| 2004/0106927 | A1 | 6/2004 | Ruffner et al. |
| 2004/0106997 | A1 | 6/2004 | Lieberson |
| 2004/0153089 | A1 | 8/2004 | Zdeblick et al. |
| 2004/0181223 | A1 | 9/2004 | Ritland |
| 2004/0204717 | A1 | 10/2004 | Fanger et al. |
| 2004/0215203 | A1 | 10/2004 | Michelson |
| 2004/0267274 | A1 | 12/2004 | Patel et al. |
| 2005/0027293 | A1 | 2/2005 | LeHuec et al. |
| 2005/0043738 | A1 | 2/2005 | Ryan |
| 2005/0043740 | A1 | 2/2005 | Haid et al. |
| 2005/0149026 | A1 | 7/2005 | Butler et al. |
| 2005/0149046 | A1 | 7/2005 | Friedman et al. |
| 2005/0267481 | A1 | 12/2005 | Carl et al. |
| 2005/0277921 | A1 | 12/2005 | Eisermann et al. |
| 2006/0030858 | A1 | 2/2006 | Simonson et al. |
| 2006/0036247 | A1 | 2/2006 | Michelson |
| 2006/0074424 | A1 | 4/2006 | Alleyne et al. |
| 2006/0084844 | A1 | 4/2006 | Nehls |
| 2006/0094951 | A1 | 5/2006 | Dean et al. |
| 2006/0122605 | A1 | 6/2006 | Suh et al. |
| 2006/0122701 | A1 | 6/2006 | Kiester |
| 2006/0122704 | A1 | 6/2006 | Vresilovic et al. |
| 2006/0136058 | A1 | 6/2006 | Pietrzak |
| 2006/0149251 | A1 | 7/2006 | Ziolo et al. |
| 2006/0167457 | A1 | 7/2006 | Suddaby |
| 2006/0235398 | A1 | 10/2006 | Farris et al. |
| 2006/0241646 | A1 | 10/2006 | Stihl |
| 2006/0247630 | A1 | 11/2006 | Iott et al. |
| 2006/0247654 | A1 | 11/2006 | Berry |
| 2006/0271198 | A1 | 11/2006 | McAfee |
| 2006/0276794 | A1 | 12/2006 | Stern |
| 2007/0118219 | A1 * | 5/2007 | Hyde, Jr. ............... 623/17.11 |
| 2007/0168043 | A1 * | 7/2007 | Ferree ............... 623/17.16 |
| 2007/0173842 | A1 | 7/2007 | Abdou |
| 2007/0233107 | A1 | 10/2007 | Zielinski |
| 2007/0233260 | A1 | 10/2007 | Cragg |
| 2007/0270851 | A1 | 11/2007 | Erickson et al. |
| 2008/0039847 | A1 | 2/2008 | Piper et al. |
| 2008/0045966 | A1 | 2/2008 | Buttermann et al. |
| 2008/0077152 | A1 * | 3/2008 | McClintock et al. ............ 606/96 |
| 2008/0269806 | A1 | 10/2008 | Zhang et al. |
| 2009/0171396 | A1 | 7/2009 | Baynham et al. |
| 2009/0187191 | A1 | 7/2009 | Carl et al. |
| 2010/0057134 | A1 | 3/2010 | Lowry et al. |
| 2010/0152784 | A1 | 6/2010 | Lowry et al. |
| 2010/0152793 | A1 | 6/2010 | Lowry et al. |

FOREIGN PATENT DOCUMENTS

| | | |
|---|---|---|
| DE | 10307758 A1 | 9/2004 |
| EP | 0890341 A1 | 1/1999 |
| FR | 2727005 A1 | 5/1996 |
| SU | 1424826 A1 | 9/1988 |
| WO | WO97/06753 A2 | 2/1997 |
| WO | WO98/14142 A1 | 4/1998 |
| WO | WO02/09626 A1 | 2/2002 |
| WO | WO02/069811 | 9/2002 |
| WO | WO 02/080789 A1 | 10/2002 |
| WO | WO03/075774 A1 | 9/2003 |
| WO | WO2006/020531 A2 | 2/2006 |
| WO | WO2006/058079 A2 | 6/2006 |
| WO | WO2007/002251 | 1/2007 |
| WO | WO2007/018458 A1 | 2/2007 |
| WO | WO2007/019631 A1 | 2/2007 |
| WO | WO2007/079242 A2 | 7/2007 |
| WO | WO2007/084427 A2 | 7/2007 |
| WO | WO2007/089858 A2 | 8/2007 |

OTHER PUBLICATIONS

Lowry et al.; U.S. Appl. No. 12/188,131 entitled "Device and method for variably adjusting intervertebral distraction and lordosis," filed Aug. 7, 2008.

Lowry et al.; U.S. Appl. No. 12/210,109 entitled "Device and method for tissue retraction in spinal surgery," filed Sep. 12, 2008.

Lowry et al.; U.S. Appl. No. 12/239,431 entitled "Vertebrally-mounted tissue retractor and method for use in spinal surgery," filed Sep. 26, 2008.

George et al.; Oblique transcorporeal approach to anteriorly located lesions in the cervical spinal canal; Acta. Neurochir. (Wien); vol. 121; pp. 187-190; 1993.

George et al.; Oblique transcorporeal drilling to treat anterior compression of the spinal cord at the cervical level; Minim. Invas. Neurosurg.; vol. 37; pp. 48-52; 1994.

Jho et al.; Anterior microforaminotomy for treatment of cervical radiculopathy: part 1—disc-preserving functional cervical disc surgery; Neurosurgery; vol. 51; supp. 2; pp. S-46-S-53; Nov. 2002.

O'Farrell et al.; U.S. Appl. No. 12/783,499 entitled "Implantable vertebral frame systems and related methods for spinal repair," filed May 19, 2010.

Lowry et al.; U.S. Appl. No. 12/323,361 entitled "Methods and systems for repairing an interverebral disc using a transcorporal approach," filed Nov. 25, 2008.

Lowry et al.; U.S. Appl. No. 13/429,246 entitled "Methods and Systems for Repairing an Intervertebral Disc Using a Transcorporal Approach," filed Mar. 23, 2012.

Choi et al.; Modified transcorporeal anterior cervical microforaminotomy for cervical radiculopathy: a technical note and early results; Eur. Spine. J.; vol. 16(9); pp. 1387-1393; Sep. 2007.

Hong et al.; Comparison between transuncal approach and upper vertebral transcorporeal approach for unilateral cervical radiculopathy—a preliminary report; Minim. Invas. Neurosurg.; vol. 49; pp. 296-301; Oct. 2006.

Jho et al.; Ventral uncoforaminotomy; J. Neurosurg. Spine; vol. 7; pp. 533-536; Nov. 2007.

Kim et al.; Anterior decompression via a wide transvertebral approach and a ceramic insert in a patient with cervical degenerative disease; Surgical neurology; vol. 67; pp. 127-134; Feb. 2007.

Wolf et al.; MBARS: mini bone-attached robotic system for joint arthroplasty; Int. J. Medical Robotics and Computer Assisted Surgery; vol. 1; No. 2; pp. 101-121; Jan. 2005.

\* cited by examiner

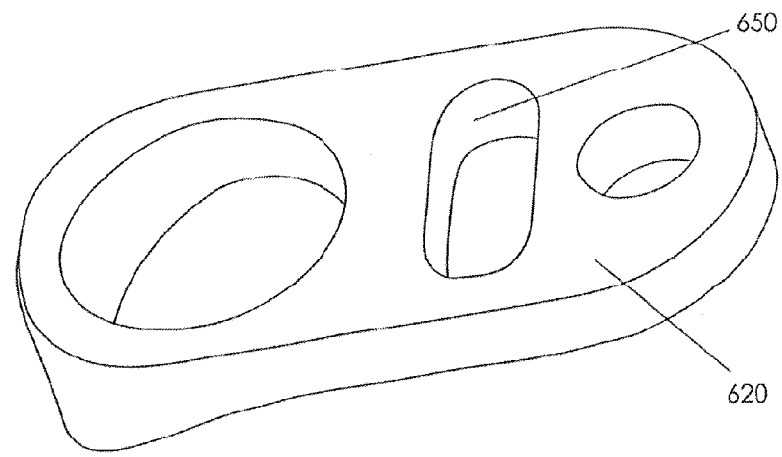
FIG. 17
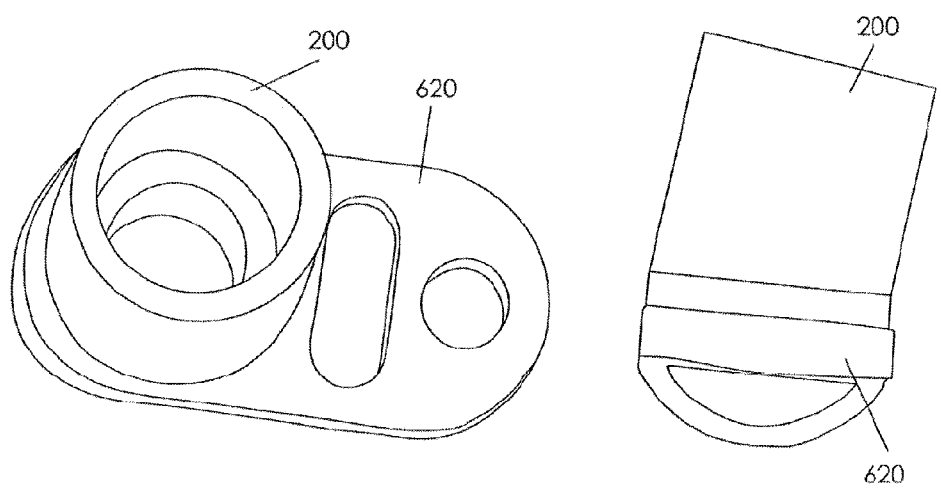
FIG. 18A
FIG. 18B

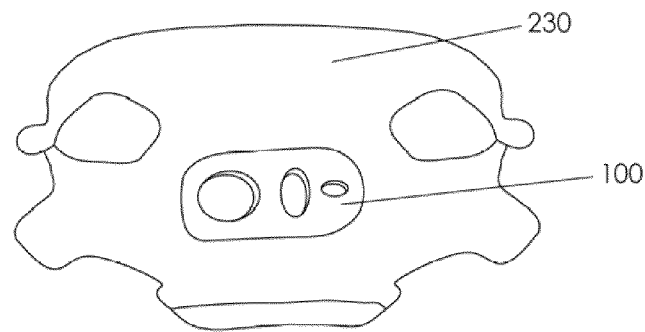
FIG. 19
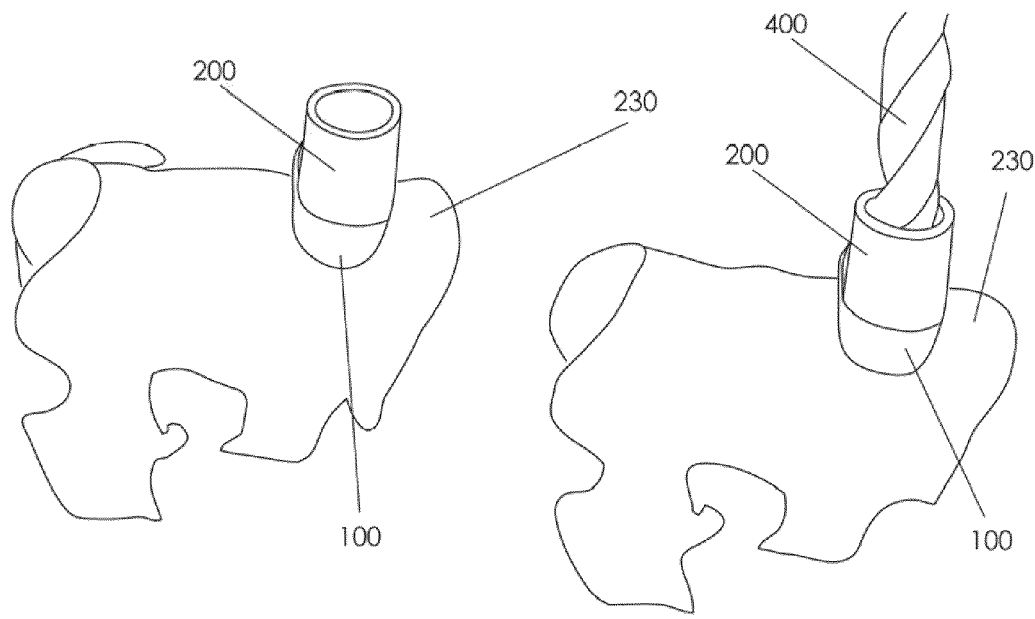
FIG. 20   FIG. 21

TRANSCORPOREAL SPINAL DECOMPRESSION AND REPAIR SYSTEM AND RELATED METHOD

CROSS REFERENCE TO RELATED APPLICATIONS

This application claims priority to U.S. Provisional Patent Application No. 60/972,192 of Lowry et al., entitled "Transcorporeal spinal decompression and repair system and related method", as filed on Sep. 13, 2007.

FIELD OF INVENTION

The invention relates to devices and methods of spinal surgery. More particularly, the invention provides an implant for use in spinal repair surgery and a method for preparing the vertebral volume to receive the implant.

INCORPORATION BY REFERENCE

All publications, patents and patent applications mentioned in this specification are herein incorporated by reference to the same extent as if each individual publication, patent or patent application was specifically and individually indicated to be incorporated by reference.

In particular, U.S. patent application Ser. No. 11/855,124 of Lowry et al. (filed on Sep. 13, 2007, entitled "Implantable bone plate system and related method for spinal repair"), U.S. Provisional Patent Application 60/972,199 of Lowry et al. (filed on Sep. 13, 2007, entitled "Device and method for tissue retraction in spinal surgery") as well as the U.S. patent application Ser. No. 12/210,109 of the same inventors and title, being filed concurrently with the present application, U.S. Provisional Patent Application No. 60/976,331 of Lowry et al. (filed on Sep. 28, 2007, entitled "Vertebrally mounted tissue retractor and method for use in spinal surgery"), and U.S. Provisional Patent Application No. 60/990,587 of Lowry et al. (filed on Nov. 27, 2007, entitled "Methods and systems for repairing an intervertebral disk using a transcorporal approach") are all incorporated by this reference.

BACKGROUND OF THE INVENTION

The performance of cervical discectomy, excision of tissue, and neural element decompression procedures have become standard neurosurgical approaches for the treatment of disorders of the spine and nervous system, as may be caused, for example, by disc degeneration, osteophytes, or tumors. The compressive pathologies impinge onto a neural element, causing a compression of nerve tissue that results in a symptomatic response such as loss of sensation or strength, occurrence of pain, or other related disorders. The majority of these procedures are performed with an anterior approach to the cervical spine. Disc and bone tissue are removed, a neural decompression is achieved, and a spinal repair procedure is performed.

The current conventional repair procedure includes a vertebral fusion in which a biocompatible implant is inserted and secured between the affected adjacent vertebrae. A bone plate is then is rigidly attached to the two vertebrae adjacent to the implant, immobilizing these vertebral segments and preventing the expulsion of the implant from the intervertebral space. Subsequently, osteogenesis of the vertebrae into the implant occurs, and ultimately the adjacent vertebrae fuse into a single bone mass. The fusion of the vertebral segments, however, can lead to problematic results. For example, the immobility of the fused vertebral joint is commonly associated with the progressive degeneration of the adjacent segments, which, in turn, can lead to degeneration of the intervertebral discs on either side of the fused joint.

Implantation of an artificial disc device offers an alternate approach to vertebral fusion. The objective of the artificial disc device is to preserve the relative motion of the vertebrae across the joint and to restore normal articulating function to the spinal column. In spite of the benefits that these procedures have brought to patients, both fusion and disc replacement have inherent problems. The surgeries are extensive, recovery time is relatively long, and there is often a loss of function, particularly with the use of fusion implants. The long-term biocompatibility, mechanical stability, and durability of replacement disc devices have not been well established. Further, there is no clinical consensus that the use of a replacement disc reduces the risk of adjacent segment degeneration.

Methods for surgery on the spine and cervical discs from an anterior approach were first developed in the 1950's, and a number of variations have been developed since then. Each anterior cervical discectomy procedure, however, has had to face the challenge represented by removing the tissue overlaying the compressing lesion (i.e., the herniated disc material, osteophyte or tumor) after having dissected through the soft tissue anterior to the spine. Early procedures exposed the compressing tissue by first making a cylindrical bone-and-disc defect in the spine centered on the disc space in sagittal and coronal planes, and generally following the plane of the disc itself. Later procedures made use of a rectangular, box-like defect in the disc space centered on the disc space and generally following the plane of the disc.

Procedures recently developed by Jho (referenced below) were motivated by the concern that procedures like those described above destroyed more of the natural disc tissue than was necessary to remove a laterally-positioned disc herniation or osteophyte (a bone spur). An alternative procedure, an uncovertebrectomy, was therefore developed that involved the removal of only the lateral-most aspect of the disc space, and the vertebral bone above and below it, which together comprise the entire uncovertebral joint. (See Choi et al., "Modified transcorporeal anterior cervical microforaminotomy for cervical radiculopathy: a technical note and early results", *Eur. Spine J.* 2007 Jan. 3; Hong et al., "Comparison between transuncal approach and upper vertebral transcorporeal approach for unilateral cervical radiculopathy—a preliminary report", *Minim Invasive Spine Surgery,* 2006 October; 49 (5):296-301; and Jho et al., "Anterior microforaminotomy for treatment of cervical radiculopathy: part 1: disc-preserving functional cervical disc surgery", *Neurosurgery* 2002 November; 51 (5 Suppl.): S46-53.) This new type of procedure allows much of the disc space to remain untouched. While preserving more of the disc space and disc material than its predecessor procedures, the uncovertebrectomy nevertheless does obliterate the uncovertebral joint, and there is concern in the field regarding the eventual development of spinal instability at that disc level. Further, drilling bone at high speed adjacent to the nearby vertebral artery and sympathetic nerve process increases the concern of a higher risk of vertebral artery, secondary soft tissue injury, and Horner's Syndrome.

In another refinement of the uncovertebrectomy procedure, an anterior cervical microforamenotomy, the uncinate process and the lateral disc tissue may be left largely intact as a hole is drilled through the bone adjacent to the disc space near the uncinate process. In both uncovertebrectomy and anterior microforamenotomy, the exposure and decompression of the neural elements generally follow the plane of the disc space. While vertebral artery injury and spinal instability remain concerns with both procedures, the risk associated with anterior microforamenotomy is considered less than that of uncovertebrectomy.

An additional refinement of both uncovertebrectomy and anterior microforamenotomy is a transcorporeal decompression procedure (also referred to as an upper vertebral transcorporeal foramenotomy or a transcorporeal discectomy) may have advantages. This procedure differs from its disc space-preserving precedent procedures in several ways. First, the axis of the access hole drilled to expose the compressing pathology (e.g., herniated disc fragment) does not parallel the plane of the disc, but instead entirely avoids the disc space plane anteriorly and captures the disc only at its most posterior aspect. Second, while uncovertebrectomy and anterior cervical microforamenotomy are applicable only to lateral pathology, the transcorporeal decompression is potentially applicable to compressing pathology located laterally in the disc space region, bilaterally, or in the midline. Further, the procedure is performed from a substantially medial position on the vertebra assuring maximal distance from the vertebral artery and other sensitive soft tissue and thereby minimizing the risk of accidental injury.

Multiple technical challenges remain, however, in optimizing the transcorporeal cervical decompression procedure for general surgical use. First, manually orienting and controlling a hand-held cutting tool to make an access channel is a subjective and error-prone procedure. The target pathology is wholly behind and/or within the bony structure of the vertebra and is not visible in any way when approached from a traditional anterior approach to the cervical spine. As the channel is essentially being driven blindly, it can easily fail to capture the targeted pathology being within the range of the posterior opening of the access channel. Consequently the surgeon needs to prolong the procedure, and explore the space by excising tissue until the pathology is found. The exploration typically leads to the access channel becoming larger than necessary and undesirably irregular, thus putting surrounding bone at risk of fracturing during or after the procedure. Given the proximity of many target pathologies to the uncovertebral joint and the vertebral artery, it is likely that exploration of the space will lead to removal of the stabilizing bone and disc tissue. This tissue damage or loss can cause spinal instability, and may further result in accidental perforation of the vertebral artery.

Second, a manual drilling process increases the risk of over penetration into the spinal canal, with highly undesirable consequences.

Third, the posterior longitudinal ligament, once exposed in the access channel, can be difficult to open. The objective is to remove the ligament cleanly from the access channel area so as to provide unobstructed visualization of the compressed neural tissue. Current surgical techniques are subjective and time-consuming, often producing a shredding of the ligament within the access channel rather than its removal therefrom, thereby impeding the visualization of the underlying target pathology or dura mater protective layer.

Fourth, currently available microsurgical instruments are not well-suited for retrieving the herniated disc or bone fragments that may be found deep to the posterior longitudinal ligament.

Fifth, after the decompression is complete, the present solutions for filling the void remaining in the vertebra are not completely satisfactory. Demineralized bone matrix putties or similar materials can fill the defect but they offer no resistance to the normal compressing or torsional forces until calcification occurs. Such materials may also impose a new source of compression on the exposed neural structures if too much putty is applied or if the vertebra deforms or sustains a compression fracture subsequently because of the absence of an implant that sufficiently resists compressive forces.

Sixth, after a solid implant plug is placed in the surgically-formed access channel, there is presently no anterior cervical plate suited to preventing its outward migration. Currently available anterior cervical plates are designed to be placed across two or more adjacent vertebrae at or near the midline, not laterally, as would be needed for lateral compressing lesions. Existing plates also are designed as motion-restriction or motion-prevention devices to be placed bridging across a disc space rather than onto a single vertebral body, consequently they are too large and are counterproductive in the application such as that described above where the objective is to preserve the articulation and relative motion of the adjacent vertebrae.

Accordingly, there is a need for a system and method whereby any compressing spinal pathology may be removed or moved so as to decompress the neural elements involved while desirably also (1) preserving native disc and bone tissue and the natural motion of the spine with natural disc material, (2) minimizing the risk of injury to the vertebral artery, (3) minimizing the risk of structural spinal instability, (4) minimizing the risk of an inadequate decompression, (5) minimizing the risk of injury to the protective dura mater layer, (6) minimizing the risk of post operative bleeding and/or (7) minimizing the risk of a subsequent vertebral body fracture due to an unrepaired defect within it.

SUMMARY OF THE INVENTION

The invention provides a system and method for forming and repairing an access channel through a vertebral body, typically a cervical vertebral body, for the purpose of gaining access to a site in need of a medical intervention. In its formation, the channel originates on the anterior surface of the vertebral body, and it then provides access from the anterior approach. The channel follows a prescribed trajectory to a prescribed exit on the posterior surface of the vertebral body, and provides an opening at the site of sufficient size to address the medical need. The access channel is typically formed in cervical vertebral bodies. The nature of the medical need typically includes the need for a decompression procedure, as may occur as a result of a problematic portion or the whole of a herniated disc, an osteophyte, a thickened ligament, a tumor, a hematoma, a degenerative cyst, or any other compressing pathology. The medical intervention may be as minimal as observing the site, or performing exploration, or it may include a diagnostic procedure, or delivering a therapy, or it may include a surgery. A typical surgery performed through the access channel can include decompressing a neural element, such an individual nerve root, a spinal cord, or a cauda equina.

The system of the invention further includes an implantable bone repair device having an external geometry complementary to the internal geometry of the access channel, and a method for repairing or healing the channel by implanting such device. Some embodiments of the device include materials that are biocompatible, biologically absorbable, or any material known to be able to substitute for bone, and to be able to be stably and effectively integrated into bone. The device may further include as well as biologically active agents, such as osteogenic agents, that promote healing of the wound represented by the access channel, and fusion of the device such that it integrates into the vertebral body.

In some embodiments, the implantable bone repair device includes an assembly with a porous body that includes actual bone tissue. Such bone tissue may be provided by the bone removed during the formation of the channel itself, or it may come from another site from the patient as an autologous graft, or it may be provided by a separate donor.

The system to form and repair an access channel includes a bone cutting tool with a cutting element, a bone plate configured to be secured to the anterior surface of the vertebral body and having an opening sized to receive the cutting element; and a trajectory control sleeve configured to detachably engage the bone plate and having a cylinder configured to receive the cutting element. The bone plate and the trajectory control sleeve, when mutually engaged, are configured to cooperate to guide the cutting element to form the access channel with a prescribed trajectory from the anterior entry to the prescribed posterior opening.

Embodiments of a method for prescribing of the point of anterior entry and the channel trajectory toward the posterior opening are typically provided by a physician who observes the cervical spine of the patient radiographically. From such observation of patient anatomy and the site of pathological interest, the physician prescribes a trajectory according to a cranio-caudal axis and a medial lateral axis with respect to a point of entry on the anterior surface of vertebral body. Such radiographic observation may occur before the attachment of the bone plate, to be summarized below, and/or after the attachment of the bone plate.

Returning to summarizing the system for forming the access channel, some embodiments include fixation elements to secure the bone to the anterior surface of the vertebral body. The bone plate may include openings to accommodate fixation elements to secure the bone plate to the anterior surface of the vertebral body. In some embodiments, the bone plate and fixation elements are configured of a biocompatible material. In some embodiments, the bone plate and the fixation elements have a composition and structure of sufficient strength that that the bone plate may be permanently implanted.

Embodiments of the trajectory control sleeve may be configured to direct the bone cutting tool on a trajectory prescribed by the method above, the prescribed trajectory being an angle according to a cranio-caudal axis and a medial lateral axis with respect to a reference plane tangential to the access channel entry on the anterior surface of vertebral body.

Embodiments of the bone plate provide a reference plane such that the trajectory control sleeve, when secured to the bone plate, may be configured with a range of angles formed on two axes with respect to the plane of the bone plate, a cranio-caudal axis and a medial lateral axis, the range of the angles varying between about 1 degree and about 30 degrees from an angle perpendicular to the plate. In typical embodiments, the range of the angles varies between about 10 degrees and about 30 degrees from the perpendicular angle. In some embodiments, the system includes a plurality of trajectory control sleeves, the sleeves varying in regard to angles formed with respect to a plane represented by the bone plate when secured thereto, the angles ranging between about 10 degrees and about 30 degrees cranio-caudally from a perpendicular angle.

In some embodiments, the trajectory control sleeve and the bone plate have mutually-engageable features that orient the engagement of the trajectory control sleeve on the bone plate in a configuration that allows the trajectory control sleeve to guide the cutting tool into the vertebral body with the prescribed trajectory. And in some embodiments, the trajectory control sleeve includes a contact surface for engaging a corresponding surface on the bone cutting tool, the surfaces configured so as to limit the penetration of the cutting tool into the vertebral body to a prescribed depth.

In some embodiments, the posterior surface of the bone plate includes one or more penetrating elements configured to impinge into the vertebral bone tissue to improve fixation and resist the torsional forces associated with bone cutting procedures. In some embodiments, the bone plate includes an anatomically-orienting feature to establish the position of the bone plate relative to the medial centerline of the vertebral body. In some embodiments, the bone plate includes a biocompatible material. And in some embodiments, at least a posterior surface of the bone plate is of sufficiently porous composition to support in-growth of bone.

In various embodiments, the bone-cutting tool is any of a drill, a reamer, a burr, or cylindrical cutting tool, such as a core cutter or a trephine. In some of these embodiments, the cutting element of the bone-cutting tool has a cutting diameter of between about 5 mm and about 7 mm.

As noted above, embodiments of the implantable bone repair device have an external geometry complementary to the internal geometry of the access channel. These bone repair device embodiments may be sized to be insertable through an opening of the bone plate, the opening also being sized to receive the bone cutting element. In some embodiments, the bone repair device includes an abutting surface configured to engage a corresponding surface of the bone plate through which it is implanted, the engagement of these surfaces adapted to prevent the bone repair device from penetrating too deeply into or through the access channel of the vertebral body. In some embodiments, the bone repair device includes receiving features in or on its anterior surface configured to accommodate the attachment of an insertion tool.

In some of these embodiments, bone repair device and the bone plate have mutually engageable orientation and locking features. In various embodiments, the locking engagement results from the application of an axial force to snap the locking feature into a corresponding retaining feature of the bone plate. In other embodiments, the locking engagement results from the application of a torsional force to engage the locking feature into a corresponding retaining feature in or on the bone plate.

In some embodiments of the surgical system the bone repair device comprises a porous cage with a porosity sufficient to permit through movement of biological fluids, such as blood, and bone cells. The composition of the porous cage portion of the device may include any of a polymer, a metal, a metallic alloy, or a ceramic. An exemplary polymer may polyetheretherketone (PEEK), which may be present in the form of PEEK-reinforced carbon fiber, or hydroxyapatite-reinforced PEEK. In some embodiments of the bone repair device with a porous cage, the porous cage device includes a closeable opening through which harvested bone material (such a native bone from the access channel site) may be passed. And in some of these embodiments, the porous cage device includes a closeable cap configured to increase pressure on the harvested bone within the cage as the cap is closed. Further, some embodiments include an internal element adapted to enhance compressive force applied to the contents of the porous cage upon application of compressive force to the cage, such force inducing extrusion of harvested bone and blood from within the cage through its porous structure to the external surfaces of the cage.

Some embodiments of the surgical system include a trajectory and depth visualization device. In some of these embodiments, the trajectory and depth visualization device includes a radio-reflective feature so as to confirm the location of the bone plate device on the appropriate vertebral body and to facilitate the extrapolation of the projected trajectory of the bone cutting tool using a radiographic image. In some embodiments, the trajectory and depth visualization device includes visual markings to indicate the distance from the point of contact with the vertebral body and cutter penetration control feature on the bone cutter guide device.

A method for performing a procedure through a vertebral body overlaying a site in need of a medical procedure includes attaching the bone plate on the anterior surface of the vertebral body, engaging the trajectory control sleeve to the bone plate, inserting a bone cutting tool through the trajectory control sleeve, and forming an access channel body by removing bone with the bone cutting tool (the channel having a centerline co-incident with the centerline of the trajectory control sleeve through the vertebral), disengaging the trajectory control sleeve from the bone plate, and performing the medical procedure through the open space provided by the access channel and the opening on the posterior surface of the vertebral body.

The access channel follows a prescribed trajectory from an anterior entry point to a prescribed opening on a posterior surface of the vertebral body in the locale of the site in need of the medical procedure. The prescription for the points of entry and exit and the vectors of the access channel are determined by radiographic observations and measurements, as summarized above. In some embodiments of the method, forming the access channel includes forming the channel with a constant, circular cross-section along a single, straight axis aligned with the trajectory control sleeve.

Before engaging the trajectory control sleeve to the bone plate, the method may include selecting the sleeve to be used in the procedure such that when the sleeve and the bone plate are engaged, the sleeve has an angular orientation relative to the bone plate that is consistent with the prescribed trajectory of the access channel. Further, before attaching the bone plate to an anterior vertebral surface, the method may include exposing one or more vertebral bodies in a spinal column by anterior incision. Further still, after performing the medical procedure, the method may include leaving the bone plate attached to the vertebral body.

In some embodiments of the method, after engaging the trajectory control sleeve to the bone plate, the method may include inserting a radiopaque locating device into the trajectory control sleeve device, radiographically observing the locating device and determining therefrom an extrapolated trajectory of the access channel toward the posterior surface of the vertebral body, and verifying that the extrapolated trajectory is consistent with the prescribed trajectory such that the point of exit at the posterior surface is proximal to the targeted site of interest.

In some embodiments of the method, after engaging the trajectory control sleeve to the bone plate, the method may include inserting a depth-measuring device into the trajectory control sleeve device to establish an optimal depth of penetration of the bone-cutting tool into the vertebral body, the depth being influenced by the disposition of the bone plate against a variable topography of the anterior surface of the vertebral body.

In some embodiments, after the completing the medical procedure through the access channel, the method further includes repairing the access channel with an implantable bone repair device, the device having an external geometry complementary to the internal geometry of the channel. In typical embodiment of the method, repairing the access channel includes implanting the bone repair device through the bone plate and into the channel. And in some of these embodiments, the method includes securing a proximal portion of the bone repair device to the bone plate.

In some embodiments of the method, repairing the access channel includes in-growing bone from the vertebral body into at least a portion of the surface of the bone repair device. And in some embodiments, repairing the access channel includes stimulating bone growth within the bone repair device by providing an osteogenic agent within the repair device.

In some embodiments of the method, repairing the access channel includes placing a portion of harvested native bone tissue within a bone repair device that comprises a porous cage. In these embodiments, the method may further include allowing or promoting intimate contact between the bone tissue within the bone repair device and bone tissue of the vertebral body. The method may further include perfusing at least some bone tissue or bone-associated biological fluid from the bone repair device into the vertebral body. Still further, the method may include healing together the harvested native bone tissue within the bone repair device and bone tissue of the vertebral body.

In some embodiments of the system, the bone plate and the trajectory control sleeve are an integrated or integrally-formed device. In this embodiment, thus the system includes a bone cutting tool with a cutting element and an integrated device comprising a bone plate portion and trajectory control sleeve portion. The bone plate portion is configured to be secured to an anterior surface of the vertebral body and has an opening sized to receive the cutting element. The trajectory control sleeve portion has a cylinder configured to receive the cutting element of the bone cutting tool, and the integrated device is configured to guide the bone cutting tool to form the access channel with a prescribed trajectory from the anterior entry to the prescribed posterior opening.

A method for performing a procedure through a vertebral body overlaying a site in need of a medical procedure with the integrated device summarized above includes attaching the integrated device on an anterior surface of the vertebral body, inserting a bone cutting tool through the trajectory control sleeve portion of the device, forming an access channel through the vertebral body by removing bone with the bone cutting tool, the access channel prescribed as summarized above, disengaging the integrated device from the bone plate, and performing the medical procedure through the access channel and the opening on the posterior surface of the vertebral body.

In some embodiments of the system and method, the bone plate or integrally formed bone plate portion does not lie directly over the anterior entry location for the access channel. Rather, the bone plate or bone plate portion is attached to the anterior surface of the vertebral body adjacent to the entry location, and supports a trajectory control sleeve or sleeve portion which may be located adjacent to the entry location.

BRIEF DESCRIPTION OF THE FIGURES

FIG. 3A shows a trajectory control sleeve in a side view.

FIG. 3B provides a side cross-sectional view of the trajectory control sleeve, showing how the angle of the sleeve relative to its base forms an asymmetrical opening in the base.

FIG. 9A is a perspective view of a trajectory pin and a drill depth gauge assembled together FIG. 9B is a perspective view of an embodiment of the depth gauge sub-assembly.

FIG. 17 is an anterior perspective view of an alternate embodiment of an implantable bone plate.

FIGS. 18A and 18B are views of the trajectory control sleeve mounted on the bone plate embodiment of FIG. 17. FIG. 18A shows the trajectory control sleeve and bone plate from a distally directed perspective.

FIG. 18B shows the trajectory control sleeve and bone plate from a side view.

FIG. 19 shows an implantable bone plate in situ on a vertebral surface.

FIG. 20 shows a perspective view of an implantable bone plate and trajectory control sleeve in situ on the vertebra surface.

FIG. 21 shows a drill cutter engaging vertebral bone tissue through the trajectory control sleeve.

FIG. 23 shows the repair device being held by a surgeon immediately prior to inserting into the access channel.

FIG. 24 shows the surgeon's finger pressing the repair device through the bone plate and into the access channel.

FIG. 25A shows the device from a proximally-directed perspective.

FIG. 25B shows the device of FIG. 25A from a distally-directed perspective.

FIG. 26A shows the device from a side view.

FIG. 26B shows the device of FIG. 26A from a proximally-directed perspective.

FIG. 27A shows the device from a proximally-directed perspective.

FIG. 27B shows the device of FIG. 27A from a distally-directed perspective.

DETAILED DESCRIPTION OF INVENTION

Figure 1:
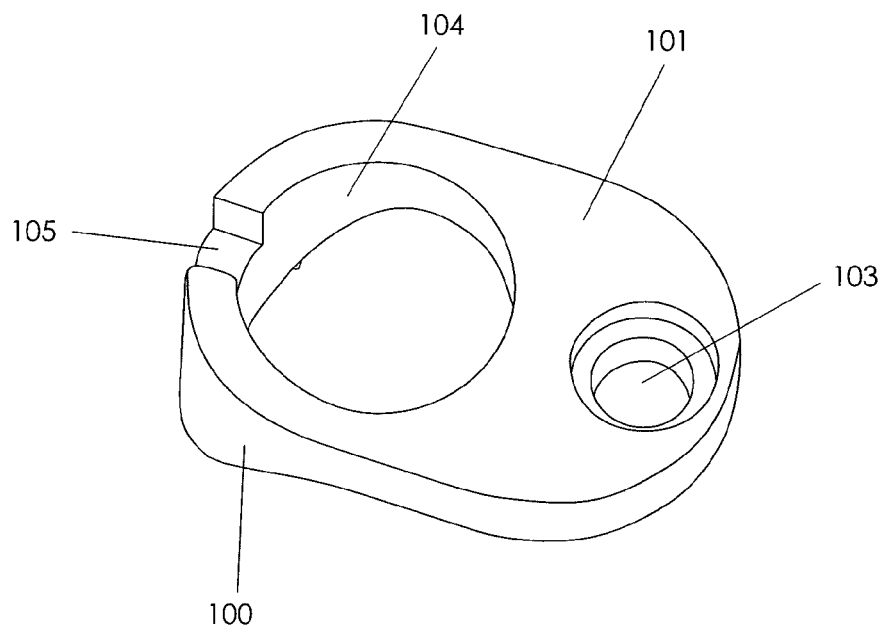
FIG. 1 is a view of an implantable bone plate device viewed from an anterior perspective.

An inventive surgical system and associated method of use are provided for transcorporeal spinal procedures that create and use an anterior approach to an area in need of surgical intervention, particularly areas at or near a site of neural decompression. Removal or movement of a source of compressing neural pathology is achieved via a surgical access channel created through a single vertebral body instead of through a disc space or through an uncovertebral joint (involving 1 or 2 vertebrae). The access channel has a specifically prescribed trajectory and geometry that places the channel aperture at the posterior aspect of the vertebra in at or immediately adjacent to the targeted compressing pathology, thus allowing the compressing neural pathology to be accessed, and removed or manipulated. The access channel is formed with precise control of its depth and perimeter, and with dimensions and a surface contouring adapted to receive surgical instruments and an implanted bone repair device.

The channel may be used to access and operate on the compressing pathology, more particularly to remove or to move a portion or the whole of a herniated disc, an osteophyte, a thickened ligament, a tumor, a hematoma, a degenerative cyst, or any other compressing pathology. As a part of the procedure, the posterior longitudinal ligament posterior to the transcorporeal access channel may be opened or removed through the access channel, thereby permitting the visualization or removal of any compressing pathology otherwise obscured by the ligament.

The invention preserves native bone and disc tissue that is sacrificed by prior art procedures, and further preserves the natural motion of the vertebral joint. The procedure also preserves at least the anterior half of the vertebral endplate of the vertebral body upon which the cutting occurs. Removal or the movement of the compressing pathology can proceed even when a portion of the compressing pathology resides beyond the limits of the transcorporeal access channel. Further, removal of the compressing pathology may occur without inducing posterior or inward compression on the dura mater protective layer surrounding the spinal cord and exiting nerve roots, or exerting direct pressure on the spinal cord or exiting nerve roots. Also, the compressing pathology removal may occur without lacerating the dura mater protective layer surrounding the spinal cord and exiting nerve roots.

Embodiments of the system and method also pertain to therapeutic occupation and repair of the vertebral body void created by making such an access channel. This repair is achieved by inserting an implantable vertebral repair device that has a conformation complimentary to the internal geometry of the access channel after the procedure is complete, and by securing the implant in the inserted position by means of a vertebral bone plate. The external surface of the vertebral repair device is in substantial contact with the internal surface of the access channel after insertion is complete, thereby substantially restoring structural and mechanical properties of the vertebrae. Such repair occurs without directly or indirectly inducing compression of underlying dura mater or neural structures. The repair further occurs without the subsequent anterior migration of the vertebral repair device, which could cause injury to soft tissue structures located anterior to the spine.

In some embodiments, the implanted device has a bioabsorbable composition that allows replacement of the implant device by in-growth of native bone tissue, or which is incorporated into the native bone tissue. As a whole the system increases the objectivity of considerations associated with spinal surgery, reduces patient risk, and contributes to better and more predictable surgical outcomes.

Various aspects and features of the invention will now be described in the context of specific examples and with the illustrations provided by FIGS. 1-37.

Figure 28:
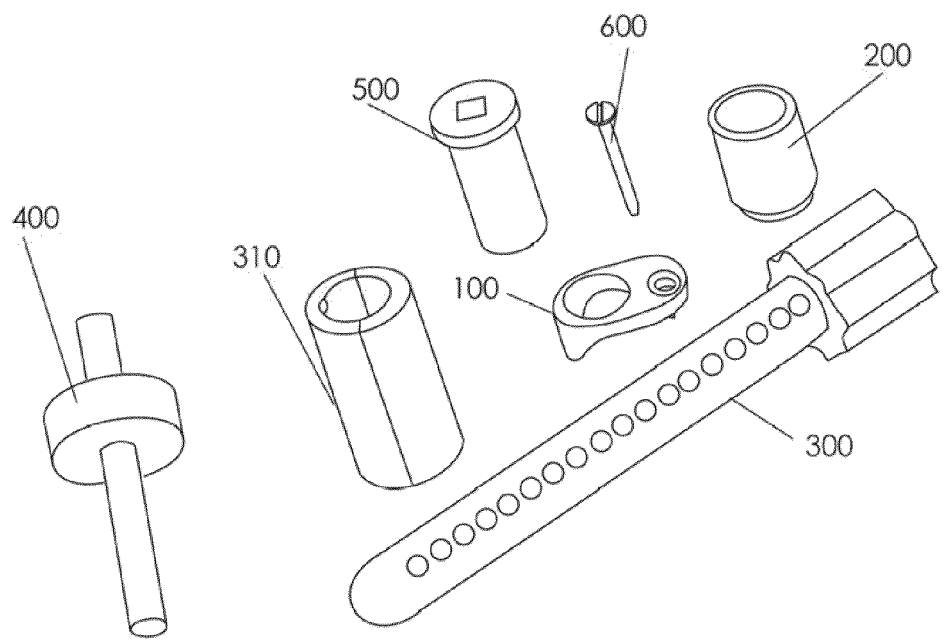
FIG. 28 shows the primary components of an exemplary system associated with the creation and repair of the intravertebral access channel.

A number of tools and instruments are included in or used within the system and methods described herein. FIG. 28 shows some of these system elements: an implantable vertebral plate 100, a cutting tool guide 200, a confirmation device or depth gauge 300, a collar 310 for the confirmation device, a cutting tool 400, an implantable device 500, and an implant locking device 600.

An implantable vertebral plate 100 is adapted to attach to the anterior surface of a vertebra. A trajectory control sleeve 200 is adapted to detachably mount the implanted bone plate 100 to establish the entry point, trajectory, and depth of an access channel created through the vertebral body. A confirmation device 300 is adapted to temporarily engage the cutter tool guide for the purposes of confirming placement of the trajectory control sleeve on the correct vertebra, for visualizing the projected trajectory of the bone cutting device, and for measuring the actual distance between the trajectory control sleeve and the anterior bone surface so as to accurately and predictably penetrate through the vertebra without impinging on the dura-mater or other neural tissue at the posterior aspect of the channel. The pin-shaped confirmation device 300 is typically radio-reflective or radiopaque, thus allowing confirmation of all geometries on a surgical radiograph taken prior to the excision of any tissue.

A cutting tool 400 is generally adapted to remove bone material and create the vertebral access channel; the tool 400 has the precise cutting geometry necessary to produce the prescribed access channel geometry within the vertebral bone. The access channel provides various forms of advantage for aspects of procedures as described further below.

A surgical cutting instrument is used to open or partially remove the posterior longitudinal ligament which can obscure a view of the pathology of interest, but becomes observable by way of the access channel. A cutting tool used to remove osteophytes (bone spurs) at or adjacent to the base of the vertebral body can be approached by way of the access channel proximal to the neural elements to be decompressed. An instrument for grasping or moving herniated disc material or other compressing pathology can be provided access to the site located at or near the base of the access channel.

An implantable bone repair device 500 is adapted repair the vacant vertebral volume created by the formation of the access channel.

An implant locking device 600 is adapted to retain the implant in the desired position. The locking device is adapted to positively engage the anterior surface of the repair implant and engagably lock it in place with respect to the implanted bone plate device 100. Fasteners such as elements 600 and 900 (seen in later figures) are applied to retain a bone plate or locking cap (see in other figures) in a desired position.

Each of these aforementioned system elements and their role in surgical procedures on the spine are described in further detail below.

Figure 2:
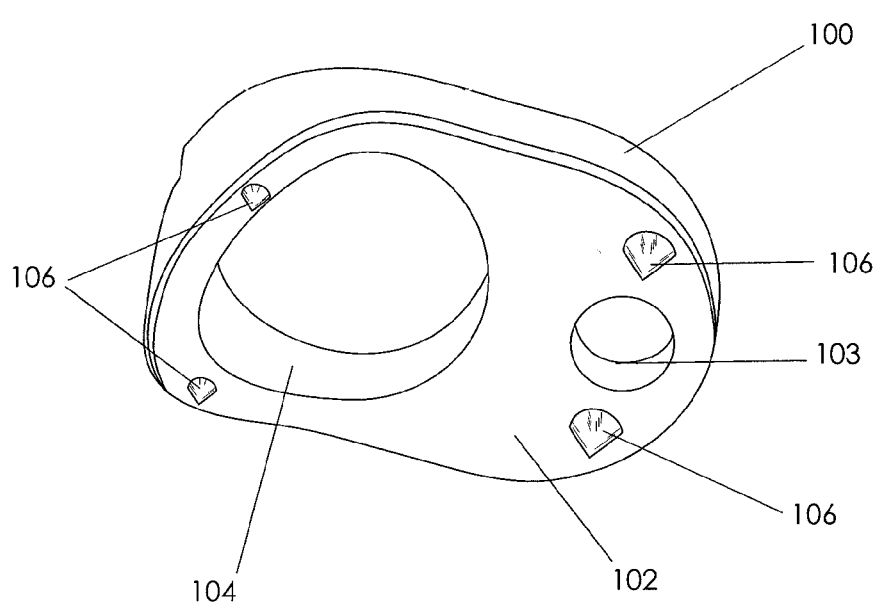
FIG. 2 is a view of an implantable bone plate device viewed from a posterior perspective.

FIGS. 1 and 2 show anterior and posterior views, respectively, of an implantable transcorporeal bone plate device 100 with a first or anterior facing surface 101 and a second or posterior facing surface 102, the posterior facing surface being configured to be proximal or in contact with the anterior surface of a vertebral body after implantation. The device further has one or more holes 103 that form an aperture between surfaces 101 and 102 to accommodate and secure retention screws there to secure the device 100 to vertebral bone.

Embodiments of implantable bone repair described and depicted herein are may include a multiple number of orifices, as for example, for inserting attachment elements, or for viewing, that have various sizes and typically are circular or ovular in form. These are merely exemplary forms and profiles of openings which may vary depending on particulars of the application of the device, such that size and profile may vary, and for example, by taking the form of any of circular, trapezoidal, multilateral, asymmetrical, or elongated openings.

The device also has a passage 104 for receiving and detachably-engaging a bone cutting guide device such as a drill or ream. The device 100 further may have one or more engaging features 105 configured to receive and engage a corresponding feature on the trajectory control sleeve in a manner that prevents relative motion of the trajectory control sleeve and its accidental disengagement from the implanted bone plate. The device may have one or more protrusions 106 on the posterior surface (FIG. 2), the protrusions being adapted to impinge into or through the cortical bone so as to increase the stability of the implant on the bone and to allow for temporary placement of the device prior to insertion of the bone screws through the opening 103. Protrusions 106 further act to stabilize the bone implant and to transfer loads around the vertebral access channel after a surgical procedure is complete, thereby further reducing the risk of bone fractures or repair device expulsion.

Figure 3A:
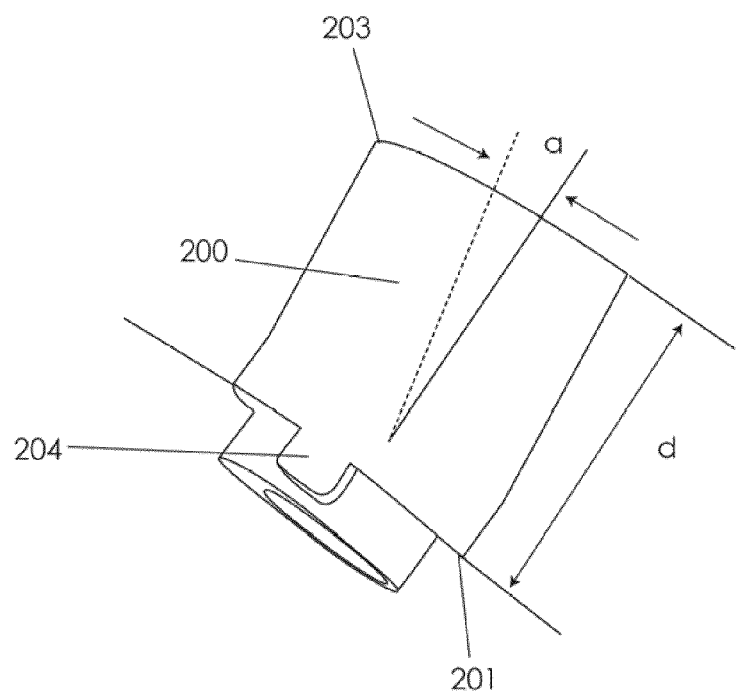
FIGS. 3A and 3B provide views of a trajectory control sleeve attachment.
Figure 3C:
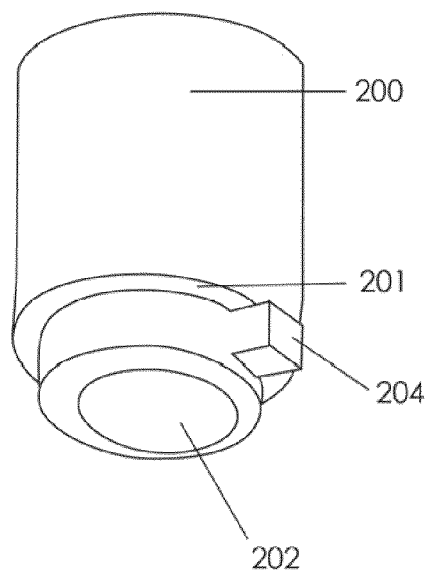
FIG. 3C shows the trajectory control sleeve from a proximally-directed perspective.
Figure 3B:
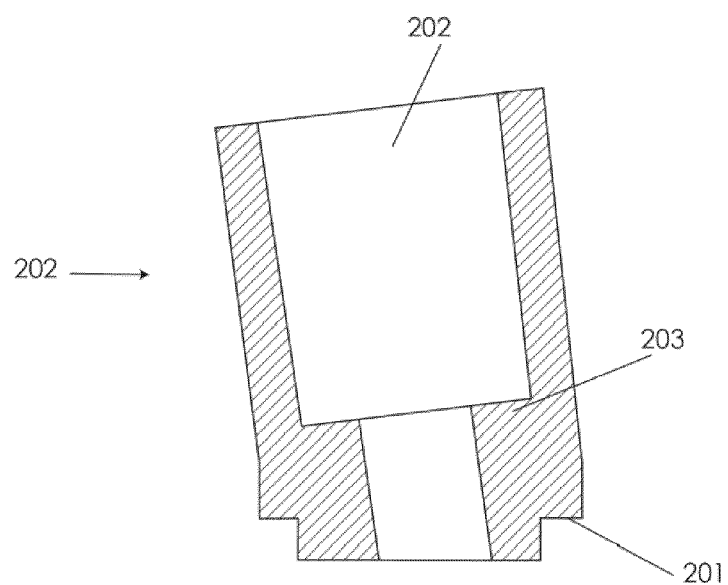

FIGS. 3A-3C show a side view and perspective view, respectively, of an embodiment of a trajectory control sleeve 200 for a bone cutting tool, a rotary cutting tool, for example, such as a drill, burr, reamer, or trephine. FIG. 3A shows a trajectory control sleeve in a side view, while FIG. 3C shows the trajectory control sleeve from a proximally-directed perspective. The trajectory control sleeve 200 has an internal cylinder 202 there through to allow passage of a bone-cutting tool, such as a drill or trephine, and to establish and control the angle α of penetration of the drill through a vertebral body. As seen in FIG. 3B the angle α refers to the angular difference from a right angle approach with respect to the plane formed by an implantable bone plate 100 to which the trajectory control sleeve is engaged. More specifically, angle α can represent a compound angle according to a cranio-caudal axis and a medial lateral axis with respect to a reference plane tangential (such as would be represented by an implanted bone plate) to the access channel entry on the anterior surface of vertebral body. The angle α is prescribed by a physician by making use of radiographic images of the spine that focus on the target vertebrae and the underlying pathology that are the subject of surgical or diagnostic interest. Such procedures are typically performed prior to surgery, and they may be repeated after the bone plate is attached to the surgical site. FIG. 3C provides a cross sectional view of an exemplary control sleeve 200, which shows the tilt of the annular ring 203 in accordance with angle α, and the consequent off-center opening at the base of the trajectory sleeve, which generally aligns with the base of the bone plate when the two components are engaged.

In some embodiments of the system and method, a transcorporal access channel is formed using a trephine type device such as those provided by Synthes, Inc (West Chester Pa.), which offers particular advantages. The trephine device produces a cylindrical channel through the vertebral bone while maintaining the core to be removed in an intact state. The core can be removed from the trephine after the tool itself has been removed from the vertebral body, and the bone tissue can be subsequently re-used as graft volume after the surgical procedure is completed.

Figure 4:
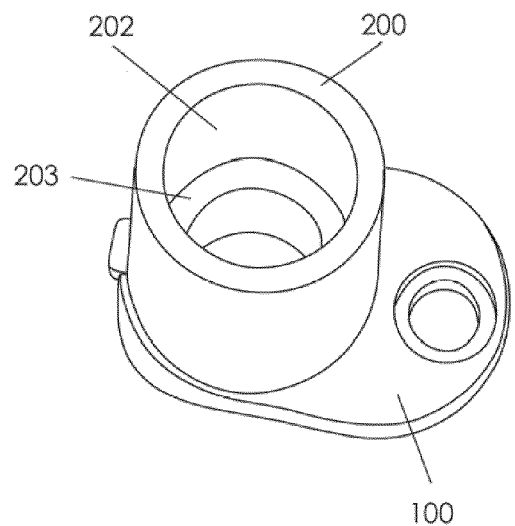
FIG. 4 is an anterior perspective of the trajectory control sleeve mounted to an implantable bone plate.

Trajectory control sleeve 200 has a surface 201 adapted to be in intimate contact with and be co-planar to an anterior facing surface 101 of a bone plate implant device 100 (after engaging the device, as in FIG. 4) so as to assure that the axial distance d is well established and controlled. The trajectory control sleeve 200 further has an annular abutting surface 203 surrounding the opening of the internal cylinder 202, the surface being adapted to positively engage a corresponding feature such as a flange or collar of the drill so as to prevent its over-penetration into the vertebral body. This abutment may be internal or external to the guide device as shown in FIG. 4 and FIG. 3A respectively. Trajectory control sleeve 200 also has an engaging and interlocking feature 204 adapted to detachably-engage a corresponding feature 105 (see FIG. 5) on the implantable bone plate 100. The trajectory control sleeve 200 is further generally adapted to protect surrounding vascular and soft tissue from accidental injury or cutting by providing a solid protective sheath around the sharp edges of the drill while it is operating.

Figure 5:
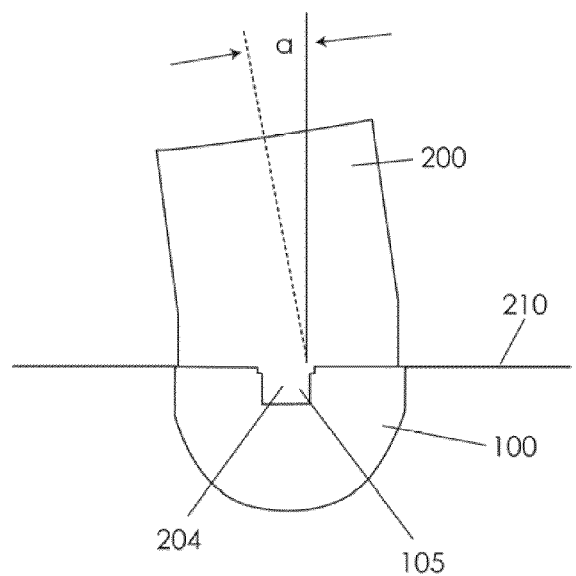
FIG. 5 is a lateral view of the trajectory control sleeve mounted to an implantable bone plate.

FIGS. 4 and 5 show a perspective view and side view, respectively, of trajectory control sleeve 200 and an implantable bone plate 100 in their mutually interlocked positions. FIG. 4 shows the internal cylinder 202 for providing access, guiding and controlling the penetration of a drill into vertebral bone. FIG. 4 further shows an alternate embodiment of the device that has an abutting surface 203, in which the abutting surface is internal to the trajectory control sleeve. FIG. 5 shows the planar engagement of the anterior surface of an implanted bone plate 101 with the corresponding surface 201 of the trajectory control sleeve. This engagement establishes a reference plane 210 from which angle α and distance d are controlled and referenced relative to the vertebral body. FIG. 5 further shows the engagement of the detachable locking features 205 of the trajectory control sleeve and of the bone plate 105.

Figure 6:
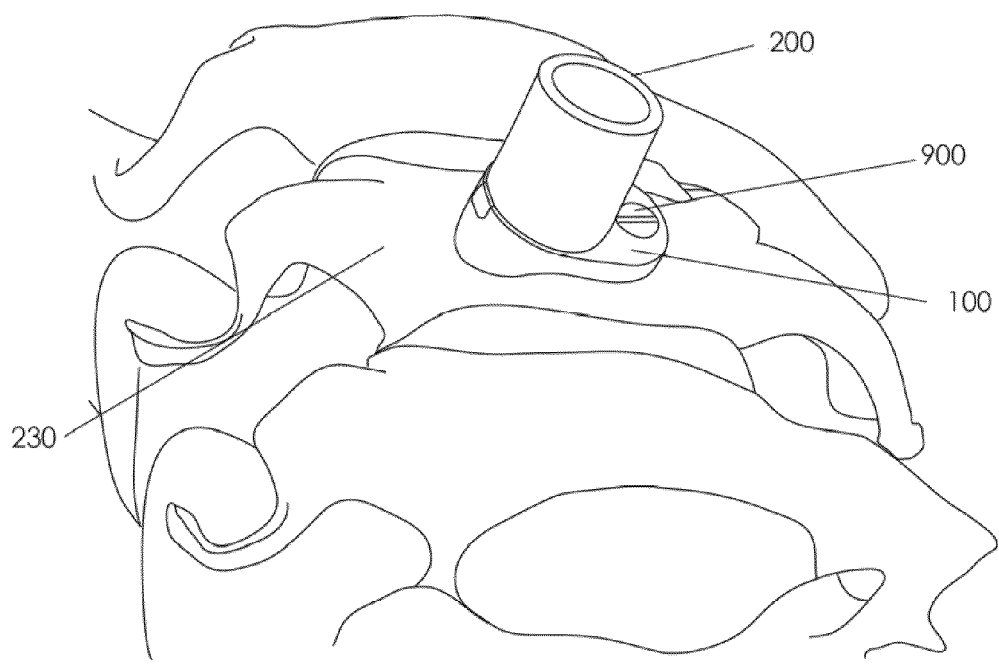
FIG. 6 is a perspective view showing an implanted bone plate screwed a vertebral body and with a trajectory control sleeve mounted thereon.
Figure 7:
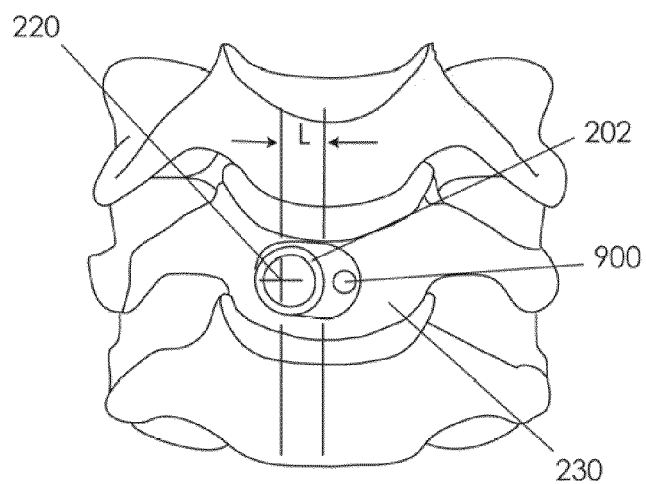
FIG. 7 is an anterior view showing an implanted bone plate screwed to a vertebral body and a trajectory control sleeve mounted thereon.
Figure 8:
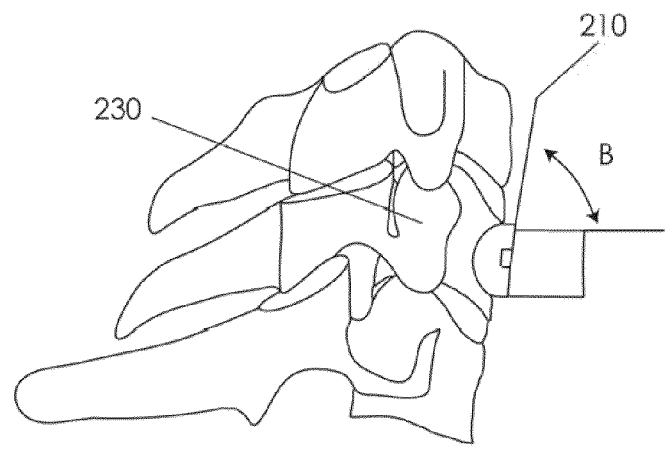
FIG. 8 is a lateral view showing an implanted bone plate screwed to a vertebral body and with a trajectory control sleeve mounted thereon.

FIGS. 6-8 relate to the placement of a mutually-engaged bone plate 100 and a trajectory control sleeve 200 to a vertebral body 230, in preparation for creating an access channel through the vertebral body. FIG. 6 provides a surface perspective view of bone plate 100 in an implanted position on a vertebral body 230, the plate secured by a bone screw 900, and further shows trajectory control sleeve 200 in its engaged position on the bone plate 100. FIG. 7 shows an anterior view of a bone plate 100 and trajectory control sleeve 200 mutually engaged and, the engaged assembly in it installed position on vertebral body 230. A bone screw 900 is inserted at or near the medial centerline 231 of the vertebral body 230, thus positioning the center point 220 of the trajectory control sleeve cylinder at a prescribed distance l from the centerline. As seen in FIG. 8, an angle β is the compliment to angle α shown in FIG. 5. After installation of the bone plate implant 100 on a vertebral body 230, the reference plane 210 may be delineated relative to the vertebral body 230 and as a baseline reference for the angle and depth of drill penetration into the vertebral body.

Figure 9A:
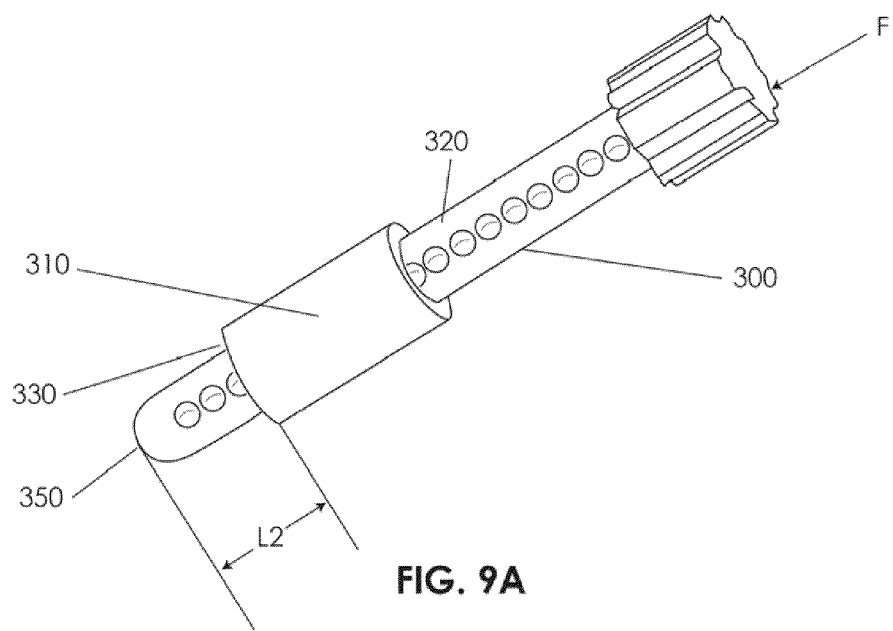
FIGS. 9A-9B show various views of a trajectory pin and a drill depth gauge.
Figure 9B:
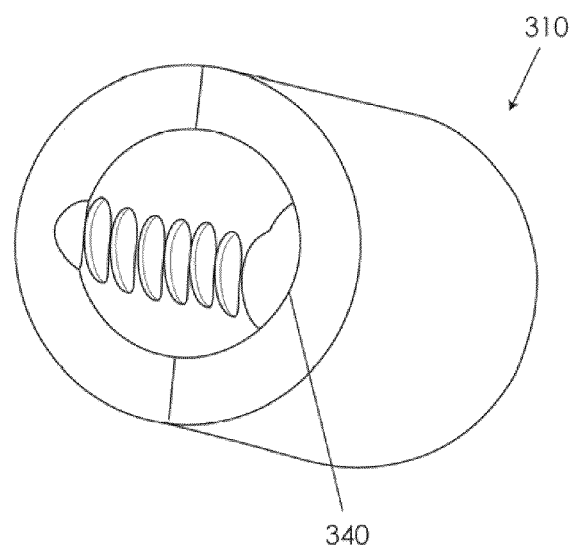

FIGS. 9A and 9B show a pin or plug type confirmation device 300 used for confirming vertebral position prior to excision of bone or other tissue and a collar 310 into which the confirmation device is inserted. A standard procedure in spinal surgery is to insert a radiographically reflective screw or pin into the vertebral body and to take an x-ray of the cervical spine prior to beginning any procedure so as to assure that the procedure is being performed at the correct vertebral level. In the embodiment described the confirmation device 300 is slidably inserted within the internal diameter of the control sleeve 200 and progressed axially therethrough until the proximal end of the device 300 is in contact with the anterior surface of the vertebral body. A radiographic image is taken inter-operatively and reviewed prior to the excision of any vertebral bone tissue. The examination includes an extrapolation of the trajectory through the vertebral body so as to confirm that the actual point of exit at the posterior surface of the vertebra is at the surgically prescribed location. Further, the axial distance from the both the anterior and/or posterior surfaces of the vertebra are measured and used as references to control the depth of bone cutting necessary to produce the access channel and to prevent over penetration into the dura mater or neural tissue. In some instances the device 300 may be used during the bone cutting procedure as a checking device to determine the actual progression of the channel across the vertebra.

FIG. 9B shows a trajectory confirmation pin 300 and a collar 310 that slidably-engages the external diameter of the pin by way of features 320 that engage complementary features 321 on the internal diameter of the collar. In this exemplary embodiment, the trajectory pin features 320 are convexities that are complementary to concave collar feature 321. Collar 310 can slide axially along the length of the pin diameter 320 and frictionally-engage the pin diameter in a manner that requires an axial force to be applied to the collar to induce axial movement. Collar 310 has a surface of engagement feature 330 that is adapted to make intimate contact with the annular surface 203 of the trajectory control sleeve when the pin is inserted into the trajectory control sleeve. Once surfaces 203 and 330 are engaged, insertion force F (FIG. 9A) applied by a surgeon causes pin 300 to travel axially through the internal diameter of collar 340, increasing the distance L2 between point 350 on the tip of the pin and the control surface 330 of the collar 310.

Figure 10:
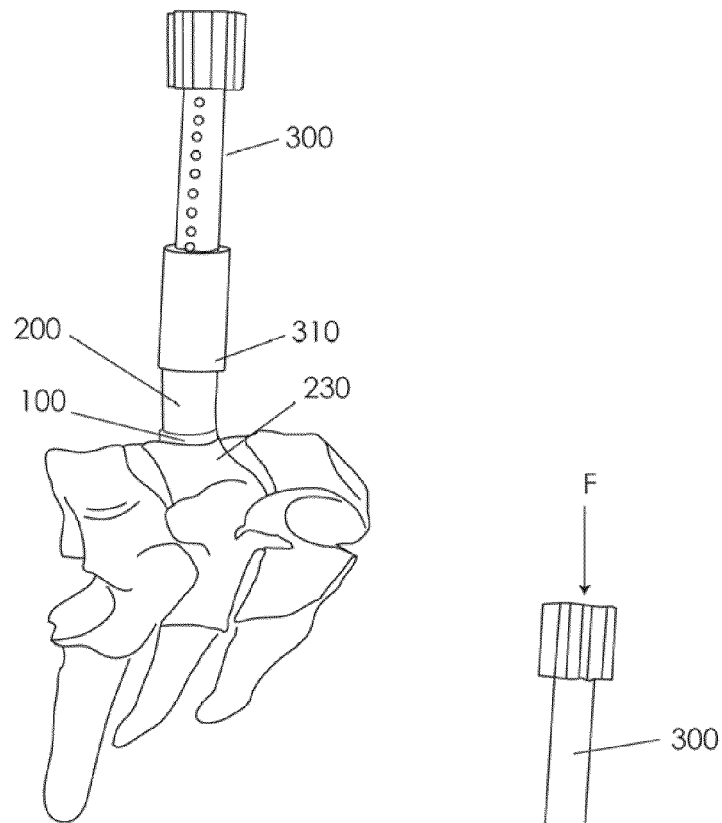
FIG. 10 is a lateral view of the trajectory pin assembly shown in FIG. 9A engaged in a trajectory control sleeve.
Figure 11:
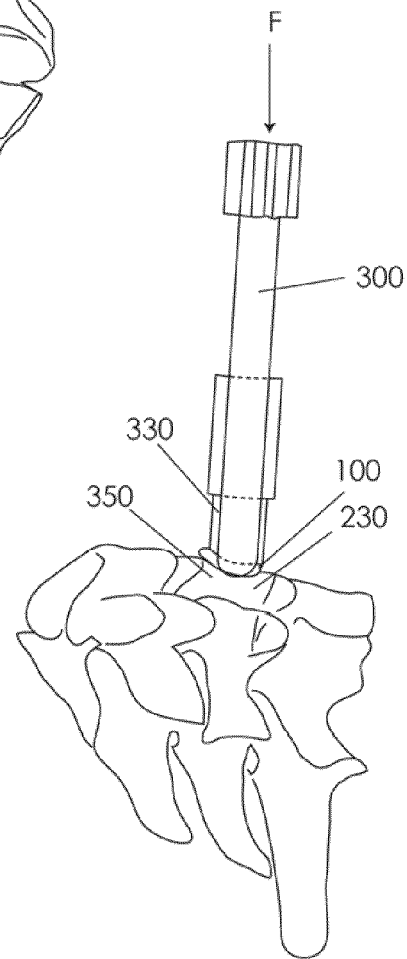
FIG. 11 is a cross sectional view showing a trajectory pin in full engagement with vertebral bone and a trajectory control sleeve.
Figure 12:
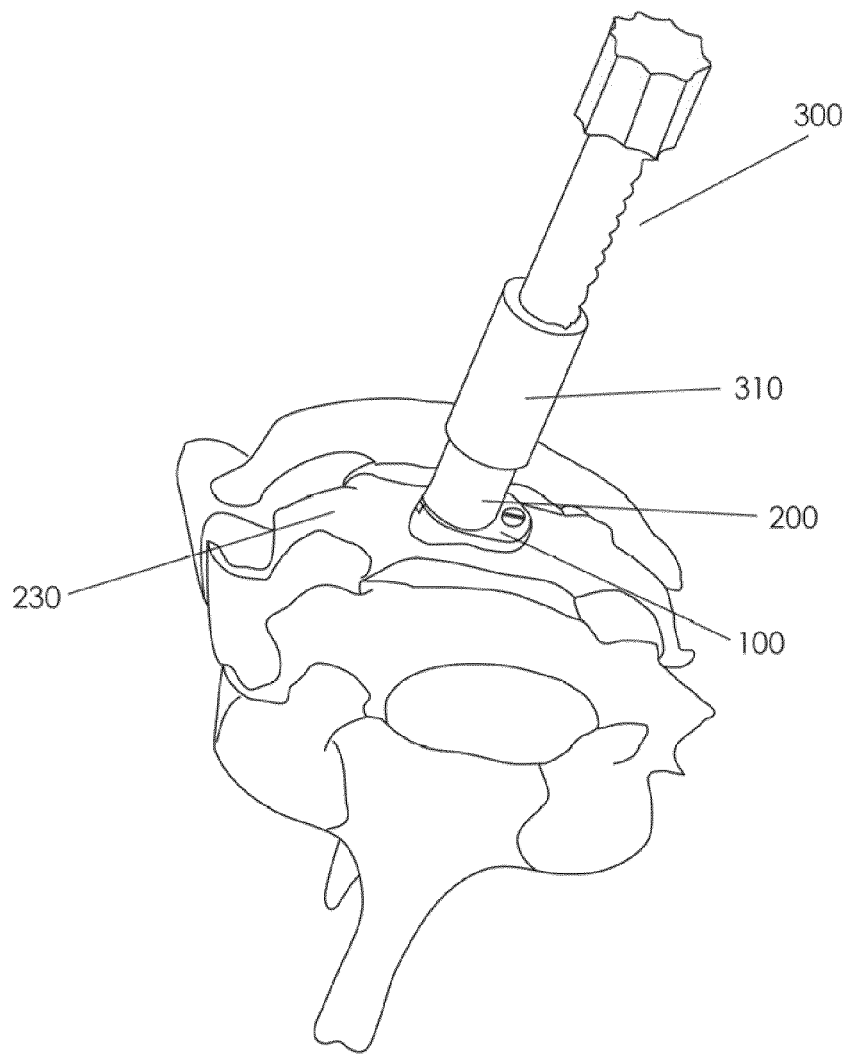
FIG. 12 is an anterior perspective view of a trajectory pin and depth gauge engaged within a trajectory control sleeve.

FIGS. 10-12 relate to the use of a trajectory confirmation pin 300, a collar 310, and trajectory control sleeve 200 in the context of a bone plate 100 in place, as implanted in a vertebral body 230. An embodiment of a pin device 300 is temporarily inserted into the internal cylinder of the trajectory control sleeve 200 and an x-ray is taken. The x-ray confirms the location of the vertebral body 230 and an anterior-to-posterior extrapolation along the centerline of the device through the image of vertebral body indicates the trajectory of the drill or cutting tool and the projected point of exit at or near the posterior longitudinal ligament. Angular and distance measurements may be made using the radiograph, and if adjustments are required, the surgeon disengages the trajectory control sleeve and installs another device with the desired geometry.

FIG. 11 shows the confirmation pin 300 at its maximum depth of penetration through the transparently rendered trajectory control sleeve 200 and bone plate implant 100. In this position, tip 350 of the pin device is in intimate contact with the surface of the vertebral bone 230. Because of the mechanical engagement of the collar 310 on the external surface, the collar remains in position relative the bone-contacting tip of the pin 350. Upon removal of the pin, distance L2 (see FIG. 9A), as measured between the collar surface 330 and the pin contact tip 350, provides a reference dimension with which the penetrating depth of the bone drill can be controlled by setting a mechanical stop that engages the annular surface 203 of the trajectory control sleeve. For ease of use, the surface of the confirmation pin 300 may have linear graduations.

Figure 13:
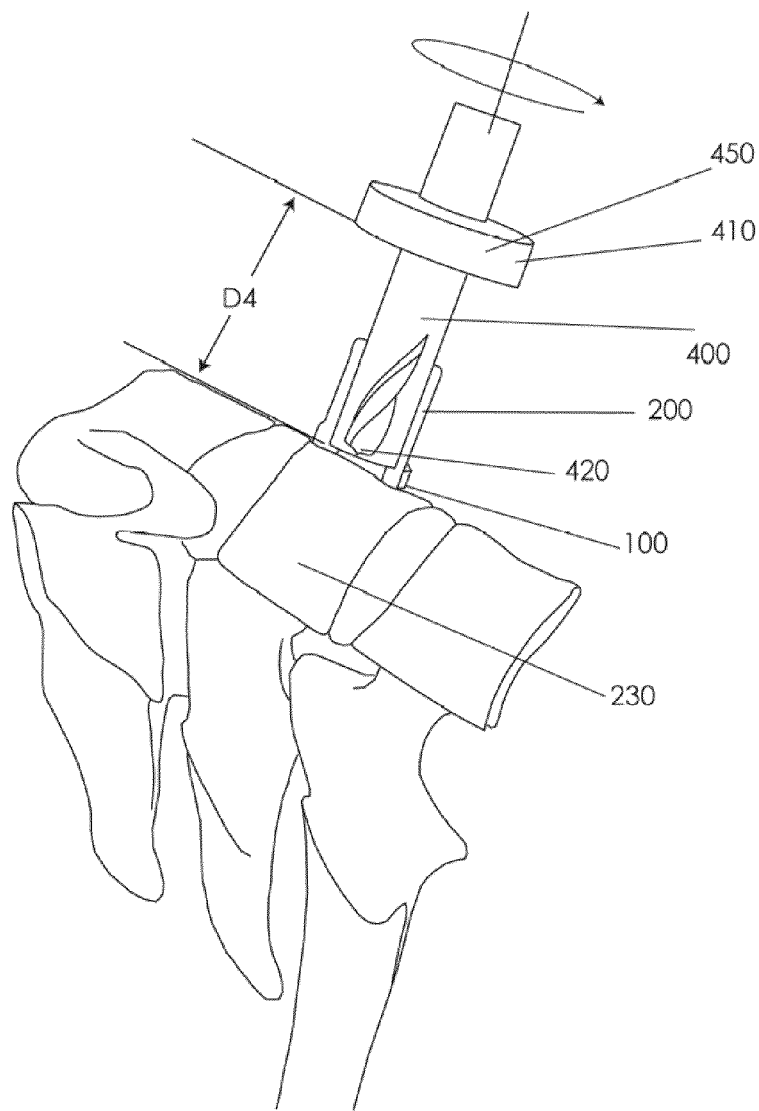
FIG. 13 is a cross section view showing a bone drill in position relative to a bone plate and trajectory control sleeve prior to cutting bone tissue.

FIG. 13 shows a bone cutting tool 400, such as a drill, burr, or reamer, inserted through the trajectory control sleeve 200 and the bone plate implant 100 with the tip of the cutting tool 420 at the initial point of contact on the vertebral body. Cutting tool 400 has a mechanical stop 450. The distance D4 from the drill tip 420 to the lower surface 430 of the drill stop 450, is a prescribed dimension equivalent to the measured distance L2 (see FIG. 9A) plus the desired depth of penetration into the vertebral body, such depth being established by the surgeon through radiographic analysis.

Figure 14:
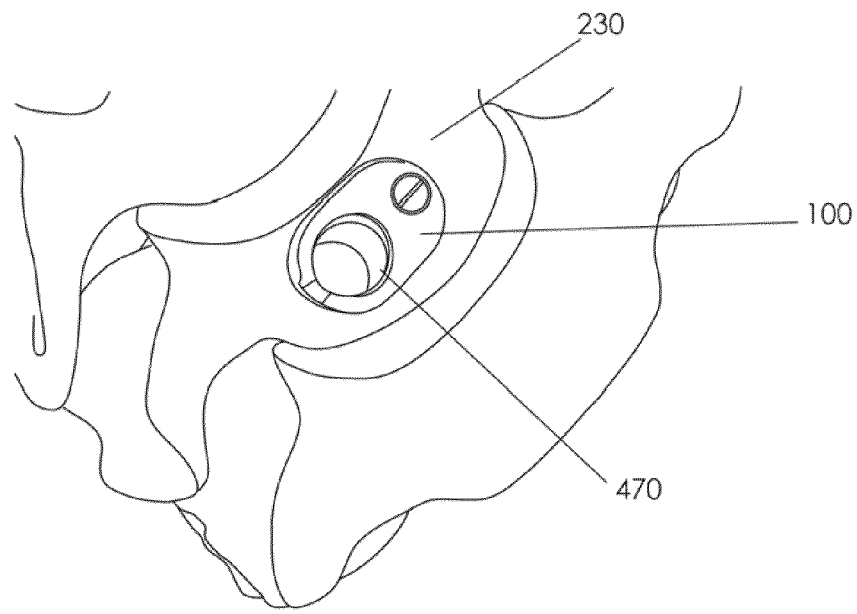
FIG. 14 is a perspective view of a bone plate after drilling has been completed and the trajectory control sleeve has been disengaged from the implanted bone plate.

FIG. 14 shows a surgical access channel 470 in a vertebral body 230, as viewed through the bone plate implant 100 after drilling has been completed and the trajectory control sleeve has been removed from the plate. After removal of the trajectory control sleeve, a neural decompression or other surgical procedure is performed through the access channel. On completion of the procedure, an intra-vertebral bone implant 500 is inserted (FIGS. 15 and 16) into access channel 470 to fill an close it, restore mechanical strength and stability to the host vertebral body 230, and to provide a medium within the vertebral body suitable for osteogenesis.

In some embodiments of the invention, the intra-vertebral access channel 470 (FIG. 14) of an implantable bone plate has a diameter of about 5 mm to about 8 mm. This size creates a surgical field that is sufficiently open enough for typical procedures, and is sufficiently large enough to minimize the possibility that the access channel will not intersect the area of neural compression. In some embodiments, the angle of entry α provided by the access channel is about 10-30 degrees, with the center of the point of entry being generally at mid-point on the cranio-caudal length of the vertebra. While these dimensions are typical, alternative embodiments of bone plate implants may have varying widths and geometries so as to accommodate wide anatomical variations. In various alternative embodiments, trajectory control sleeve devices also may include a wide range of angles and depths for the same reason.

Figure 29:
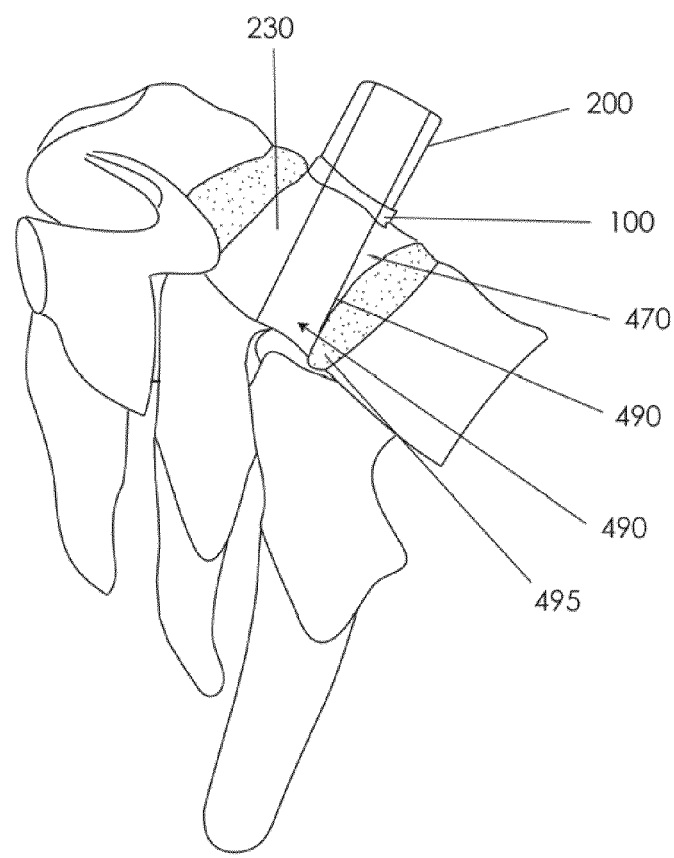
FIG. 29 shows a typical access channel that may be produced with the inventive systems and methods.

With a combination of the angle of entry, the point of entry into the vertebral body, and the size of drill used to create the access channel 470, some embodiments may result in a penetration of the posterior disc space in the posterior 20%-30% of the disc volume 480, leaving the vertebral end plate 490 and the native disc tissue 495 substantially intact. FIG. 29 illustrates a typical access channel 470 that may be formed using a 6 mm drill diameter, about a 10 degree angle of entry, with an entry point on the cranio-caudal centerline of the vertebral body.

Figure 15:
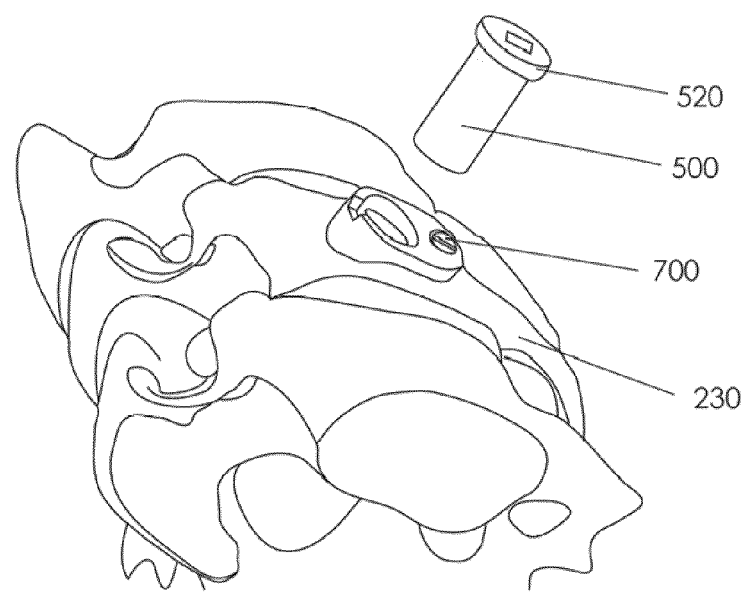
FIG. 15 is a perspective view of a spinal repair implant in the pre-insertion position relative to the implanted bone plate.
Figure 16:
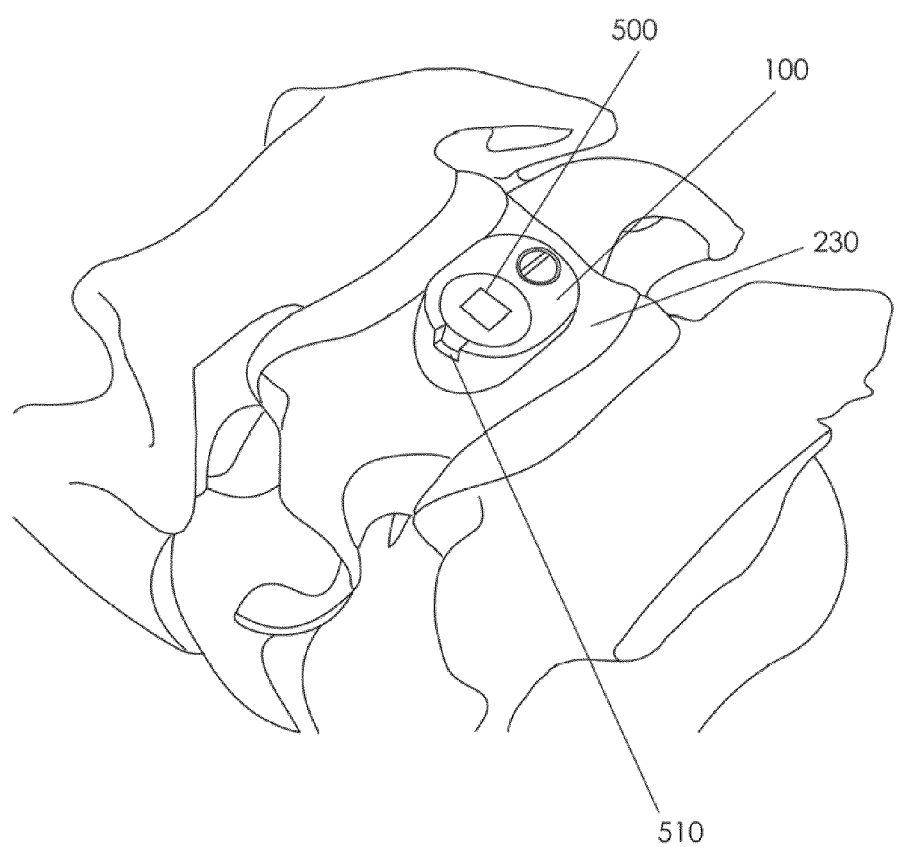
FIG. 16 is a perspective view of a spinal repair implant installed into an access channel through an implanted bone plate.

FIG. 15 shows an intra-vertebral implantable bone repair device 500 positioned for implantation within the vertebra 230 through the bone plate implant 100. Various embodiments and features of a bone repair device are described in U.S. Provisional Patent Application No. 60/990,587 of Lowry et al. (filed on Nov. 27, 2007, entitled "Methods and systems for repairing an intervertebral disk using a transcorporal approach"), which is incorporated herein in its entirety by this reference. In the embodiment shown, implant 500 has an abutting surface 520 adapted to engage with a corresponding surface of the bone plate implant. This arrangement prevents excess penetration of the implant through the access channel and prevents the implant from compressively engaging neural elements. FIG. 16 shows the implantable device 500 in the final installed position relative to the bone plate 100. The device 500 has a locking mechanism 510, such as a conventional bayonet mount, for engaging the bone plate in order to prevent migration of the implant within or out of the access channel.

FIG. 17 shows an alternative embodiment 620 of an implantable bone plate as previously described and shown in FIGS. 1 and 2. In this present embodiment, bone plate 620 has a larger lateral dimension to accommodate particular anatomies that may be encountered, including those of patients, for example, with small stature, degenerative bone conditions, or osteophytes or other abnormalities that may require alternate fixations. To assure accurate location of the device relative to the medial centerline of the vertebra, implant device 620 may include a viewing port 650 or some other positioning indicator. FIGS. 18A and 18B show anterior perspective and side views, respectively, of the engagement of a trajectory control sleeve 200, as previously described, with the alternative bone implant device embodiment 620.

In another alternate embodiment, an implantable bone plate and bone cutting device may be formed as a unitary device and temporarily fixed to the vertebral body. In this embodiment an intra-vertebral access channel is created using the temporarily implanted device; subsequently, the device is removed, the surgical procedure performed, and the access channel repaired using the intra-vertebral implant as previously described. In this embodiment, a bone cutting device may have a least two cutting diameters or widths, the first being that necessary to produce the access channel, the second being a larger diameter configured to remove an annulus of bone on the anterior vertebral surface so as to provide an abutting surface against which the implant would rest in order to prevent over-penetration of the intra-vertebral repair implant within the vertebra.

Figure 22:
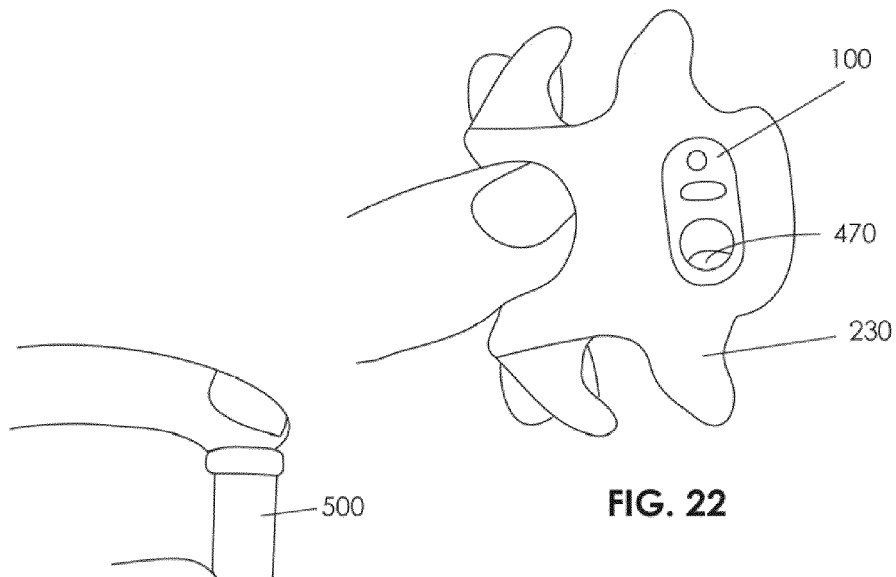
FIG. 22 shows an access channel through an implanted bone plate and into vertebral bone tissue.
Figure 23:
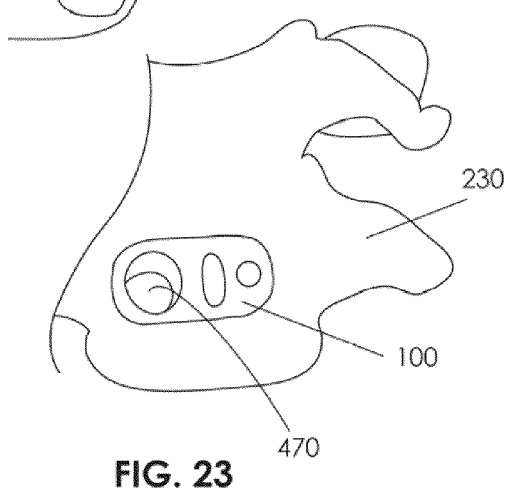
FIGS. 23 and 24 show an intra-vertebral repair device engaging vertebral bone through the bone plate.
Figure 24:
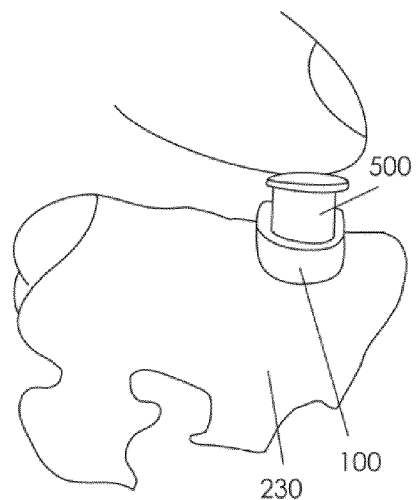

FIGS. 19-24 show exemplary devices being put to exemplary use to evaluate the practical viability, fit, and the functionality of methods for their use. FIG. 19 shows an implantable bone plate 100 in situ on a vertebral surface 230. FIG. 20 shows a perspective view of the implantable bone plate and trajectory control sleeve 200 in situ on the vertebral surface. FIGS. 21-24 include a view of surgeon's finger to show scale and feasibility of manual manipulation of elements of the inventive system. FIG. 21 shows a bone cutting tool 400 engaging vertebral bone tissue through the trajectory control sleeve 200. FIG. 22 shows an access channel 470 through the implanted bone plate and into vertebral bone tissue. FIG. 23 shows an intra-vertebral repair device 500 being readied for engaging vertebral bone through the bone plate 100.

Figure 25A:
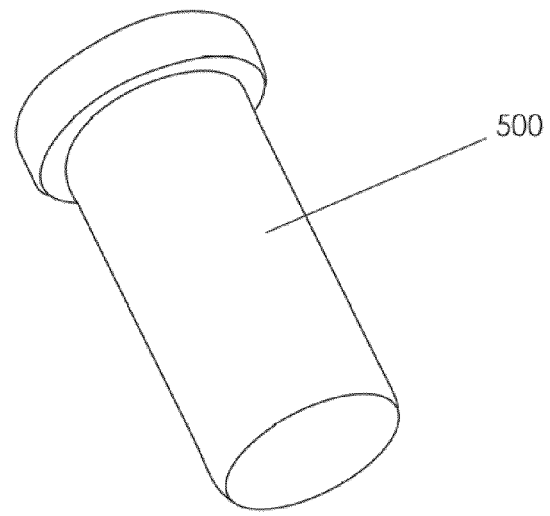
FIGS. 25A and 25B show views of an intravertebral repair device embodiment with a proximal abutting surface orthogonal to the body of the device.
Figure 25B:
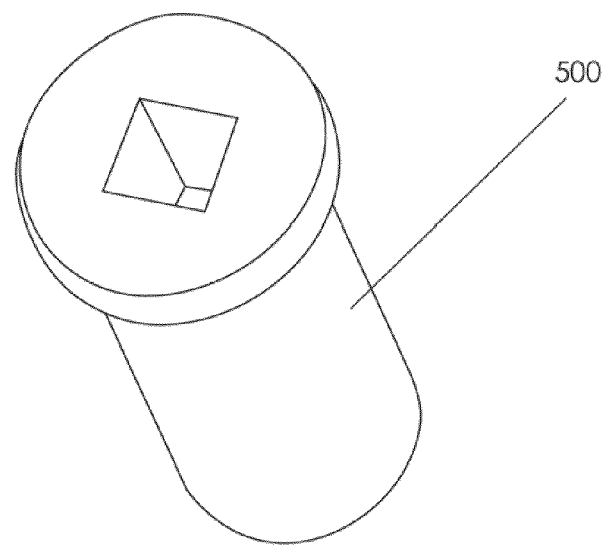
Figure 26A:
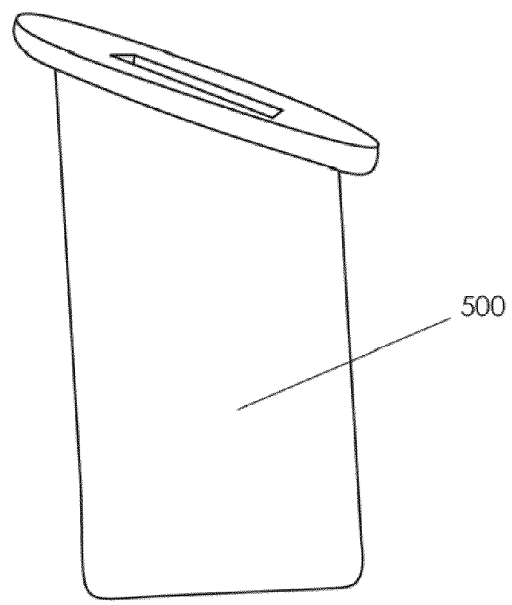
FIGS. 26A and 26B show views of an intravertebral repair device embodiment with a proximal abutting surface canted with respect to main axis of the body of the device.
Figure 26B:
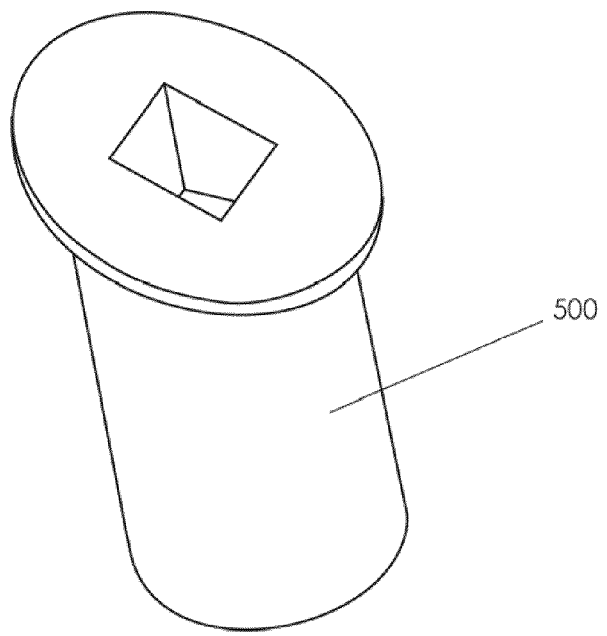
Figure 27A:
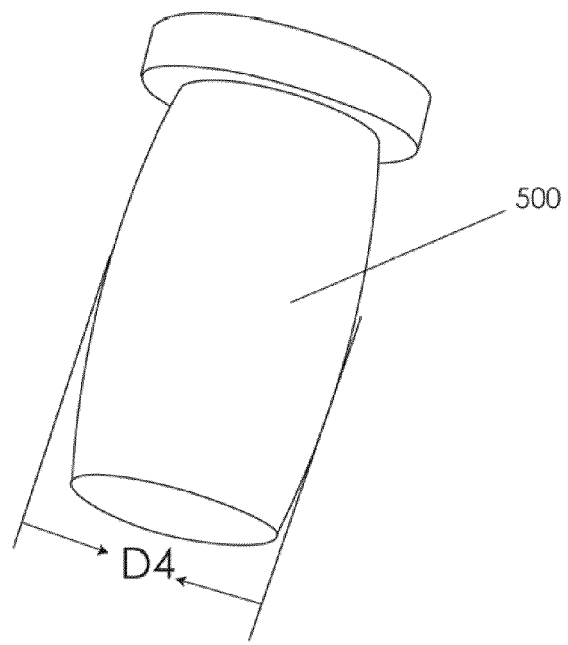
FIGS. 27A and 27B show views of an intravertebral repair device embodiment with a convex external profile, wider in its central portion, narrower at proximal and distal ends.
Figure 27B:
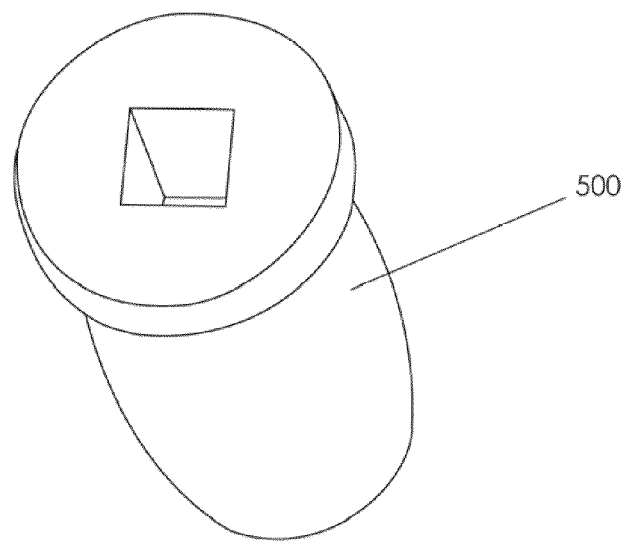

FIGS. 25A-27B show embodiments of alternative external geometries of the intra-vertebral implantable devices 500 as may appropriate for particular patients or procedures. FIGS. 25A and 25B show views of what may be considered a default embodiment of an intravertebral repair device with a proximal abutting surface orthogonal to the body of the device. FIG. 25A shows the device from a proximally-directed perspective, while FIG. 25B shows it from a distally-directed perspective. FIGS. 26A and 26B show and embodiment wherein abutting surface 520 is canted at an angle not orthogonal to the central axis of the device 500. FIGS. 27a and 27b show an intra-vertebral implant device 500 with a convex external profile where dimension D4 is nominally larger than the internal diameter of the access channel so as to compressively engage the cancellous bone tissue. Such a compressive engagement can improve the interference fit of the device therein and to inter-diffuse cancellous bone tissue within the implant volume to improve osteogenesis.

FIG. 28 shows an assemblage of some of these system elements, and was described at the outset of the detailed description; shown is an implantable vertebral plate 100, a cutting tool guide 200, a confirmation device or depth gauge 300, a collar 310 for the confirmation device, a cutting tool 400, an implantable device 500, and an implant locking device 600. FIG. 29 provides an exemplary embodiment of the invention that was discussed earlier in the context of the formation of an access channel, in conjunction with associated description of FIGS. 14-16.

Implantation of the patient's own bone tissue (an autologous graft) is a generally advantageous approach to repairing bone, as autologous grafting typically yields high success rates and a low rate of surgical complications. Accordingly, some embodiments of the invention include using core bone tissue harvested from the forming of the access channel, and implanting the plug, intact, in the form of bone repair graft. An advantage to recovering and making use of bone derived from the channel includes the absence of a need to harvest bone from a second site. Embodiments of the invention, however, do include harvesting bone from secondary sites on the patient, such as the iliac crest, as may be appropriate in the practice of the invention under some circumstances. In some embodiments, for example, it may be advantageous to supplement bone derived from the access channel with bone from other sites. In still other embodiments, under various clinical circumstances, it may be appropriate to make use of bone from donor individuals. Bone from other autologous sites or other donor individuals may be used as a repair device in the form of an appropriately formed plug, or bone may be fragmented or morselized, and packaged as a solid plug, or bone may be included as a preparation provided in a porous cage, as described further below.

Some embodiments of methods provided make use of a trephine type bone cutting system, as noted above. With a trephine bone cutting system, the external diameter of the bone tissue core is about equal to the internal diameter of the trephine device, while the internal diameter of the access channel is about equal to the external diameter of the device. Thus, a trephine-derived bone plug from forming the access channel provides an appropriately-sized piece to be inserted into the channel for repair and healing, but does not necessarily make intimate contact with the inside surface of the channel due to the width of the kerf created by the trephine.

Optimal healing and recovery from implantation of bone material into an access channel occurs when there is an intimate or compressive engagement of the graft material with the vertebral bone tissue (substantially cancellous bone), as this intimate association provides for rapid blood profusion and bone healing while providing mechanical support during healing. Accordingly, an embodiment of the bone repair device provided herein includes a device with bone tissue inside a porous cage, as described in detail below.

The porosity of the cage is a particularly advantageous feature for allowing cell to cell contact through the boundary of the device. To some degree, it may also allow cell migration, however the most advantageous factor in promoting rapid healing is cell to cell contact that initiates sites of tissue unification, which can then spread, stabilize a healing zone around the graft or bone repair device, and ultimately lead to effective fusion and integration of the graft within the host vertebral body.

A porous cage, as provided by this invention, also has a compressibility, such that when the contents of the cage are subject to a compressive force, however transient and minimal, blood or plasma and bone cells that are present in the harvested cancellous bone are forced outward into the environment within and around the access channel site. Extrusion of biological fluid in this manner, advantageously packs bone tissue closer together within the cage, and bathes the periphery of the graft and the host-graft intersectional zone with a medium that is optimal for exchange of dissolved gas and nutrients that are critical in the initial stages of healing. Some embodiments of the invention include bathing the bone tissue preparation in a supportive liquid medium before implantation. Such bathing may occur prior to placing the bone tissue preparation in the porous cage and/or after placing the preparation in the cage. The liquid medium may be any appropriate cell culture medium, and may be further supplemented with biological agents, such as osteogenic agents or other growth factors.

Embodiments of the implantable porous cage bone repair device, as provided herein, encapsulate the bone tissue contained therein, and provide mechanical stability to the access channel during healing. These embodiments compensate for the volumetric loss associated with the bone cutting process of the trephine and promote contact between the bone volume within the device and the surrounding vertebral bone tissue. The device, as a whole, and like other bone repair embodiments provided, cooperates with the implanted bone plate so that the orientation and penetration depth of the implant device within the access channel may be controlled. These forms of control assure that the device does not over-penetrate through the channel, thereby compressing the dura mater or neural elements within the vertebra, and assuring that the implanted device cannot migrate in an anterior direction out of the access channel.

Exemplary embodiments of the porous cage device and associated method of use will now be described in further detail, and in the context of FIGS. 30-37.

Figure 30:
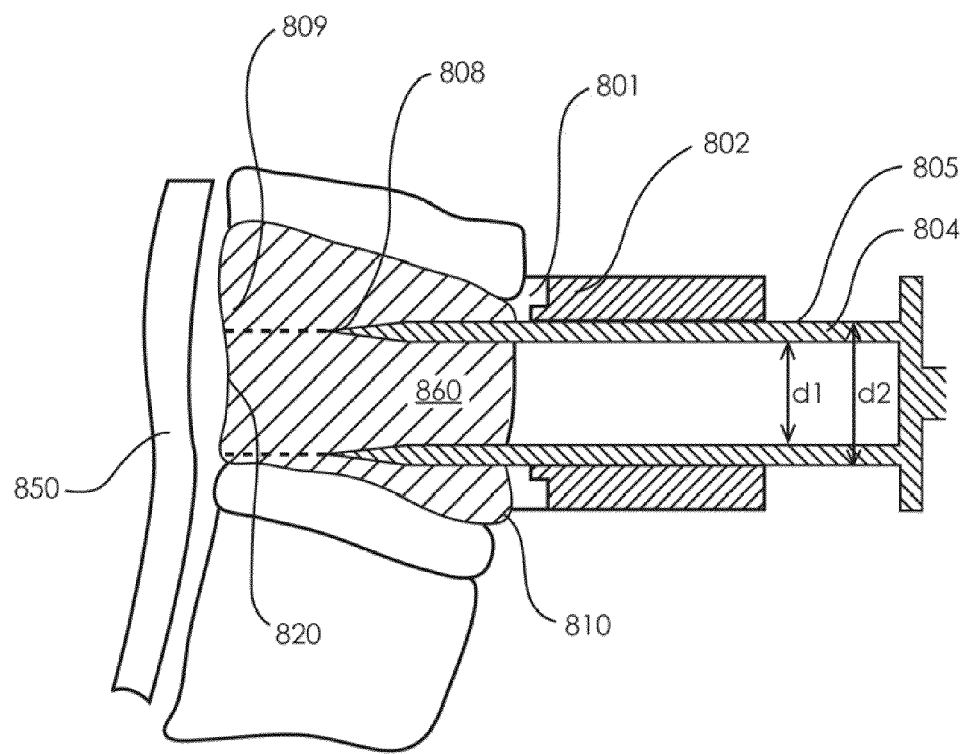
FIG. 30 shows a cross sectional view of an access channel being formed in a vertebral body with a hollow cutting tool, a trephine, which forms an access channel with a removal bone plug.

FIG. 30 provides a cross-sectional view of a vertebral body 809 with a bone plate 801 attached to the anterior bone surface 810. Mounted on the bone plate is a trajectory control sleeve 802 cooperating with the bone plate 801 to establish and control the trajectory of a bone cutting tool 804 with a cutting surface 808 through the vertebral body to direct the trajectory of the formed access channel to a prescribed point of exit at the posterior surface of the vertebra 820, in the locale of a site of medical interest.

The depicted exemplary bone cutting tool 804 is a hollow bone cutting tool, a trephine, with an external diameter 805 selected to be complementary to the internal diameter of the trajectory control sleeve 802, and to cooperate therewith so as to assure that the centerlines of the bone cutting tool and the trajectory control sleeve are substantially co-incident during the bone cutting process. The trephine 804 progresses through the vertebral body 820 from an anterior to posterior direction until the cutting surface 808 penetrates the cortical bone at the posterior surface of the vertebra proximal to the spinal cord 850. Upon removal of the trephine from within the vertebral body, a core of bone tissue within the interior of the trephine is extracted from the wound opening, thus creating or exposing an open access channel from the anterior surface of the vertebral body to the neural elements and the prescribed site of medical interest immediately behind the posterior wall of the same vertebral body.

Figures 31, 32:
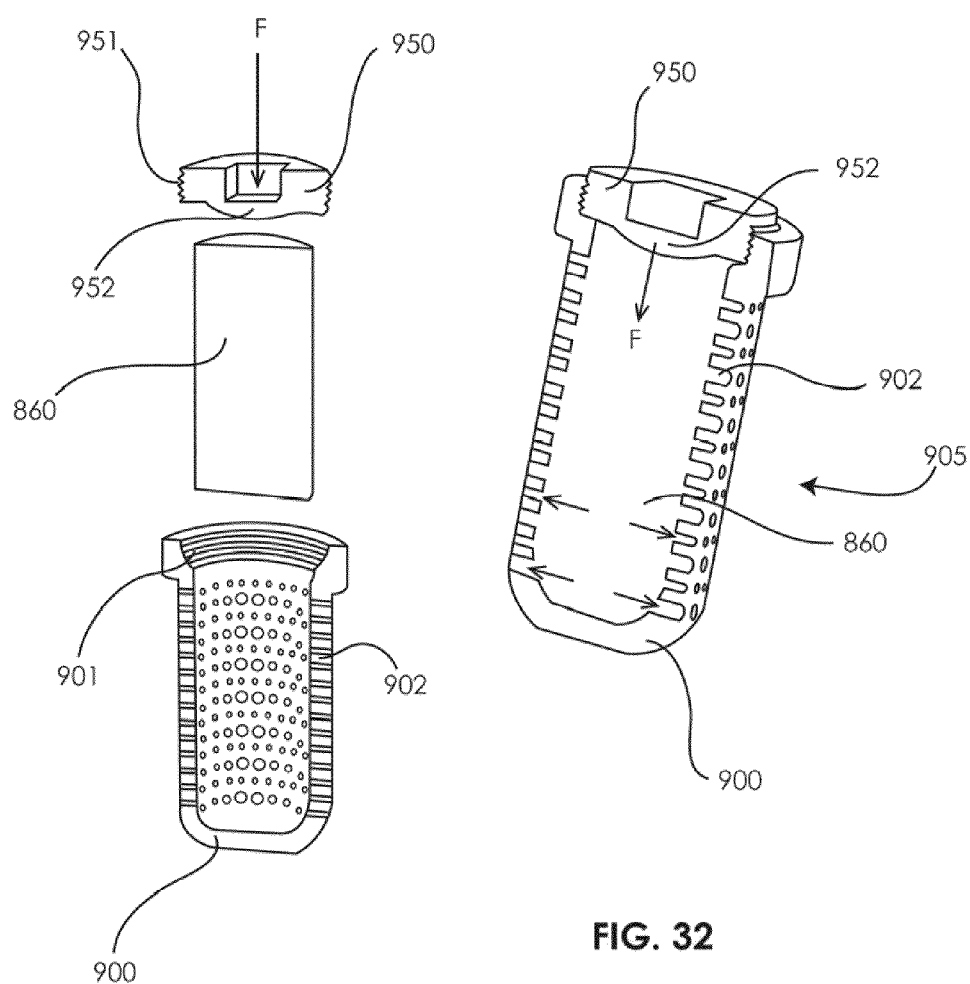
FIG. 31 shows an exploded view of a bone repair device with a porous body configured to hold bone tissue, and to allow compression of the tissue upon closing the porous body.
FIG. 32 shows a cut away cross sectional view of the bone repair device of FIG. 31 in assembled form.

FIG. 31 shows components of an exemplary bone repair device in a linearly exploded view from an external perspective. At the top, a cap 950 is above a vertebral bone core 860; the bone core is positioned for placement in a porous cage 900. FIG. 32 is a cross-sectional view of the fully assembled device 905. According to the inventive method, the vertebral bone core 860 is placed within an implantable intravertebral bone repair device 900 with a porous wall, and encapsulated by a cap or closing element 950. In this exemplary embodiment the cap has a screw thread 951 disposed to engage a mating thread 901 on the body 900 of the implantable device; the cap further has a compression element 952 disposed to exert a compressive force F on the bone graft core 860 when the cap is being closed on the body 900 of the repair device, and consequently inducing extrusion of native tissue within the device, through open pores 902 contained within the perimeter wall of the implant device. As described above, the bone tissue placed within the body of the repair device is not necessarily an integral bone plug intact from the trephine used to form the channel; the bone tissue may be a fragmented or morselized preparation, it may include bone from another site on the patient, and it may include bone from another donor.

Figure 33:
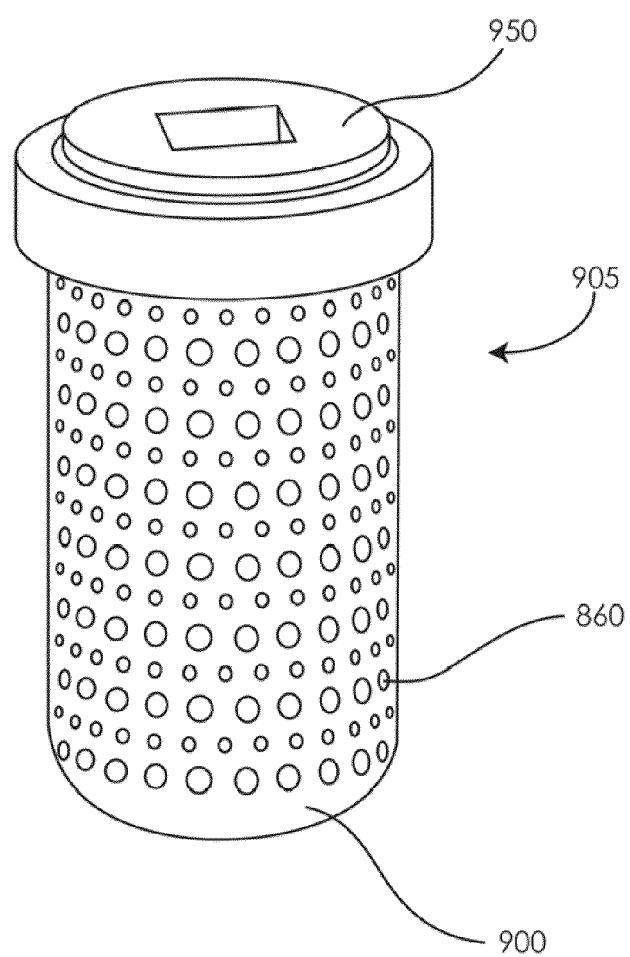
FIG. 33 shows an external view of the assembled bone repair device of FIG. 33 with bone tissue and associated fluid being extruded under pressure.

FIG. 33 provides an external perspective view of an assembled bone repair device 905. This view captures a moment shortly after the cap 950 has been closed, and by such closing has increased the pressure on the bone tissue contained within the device. By virtue of this elevated pressure within the porous walled body 900, bone core graft tissue and associated biological fluid are extruding through the porous perimeter wall. In some embodiments of the method, the cap 950 is closed on the porous body 900 of the repair device immediately prior to insertion of the assembled device 905 into the access channel within the host vertebral body, and in some embodiments of the method, the cap is closed after insertion of the porous body 900, thereby forming the complete assembly 905 in situ.

Figure 34:
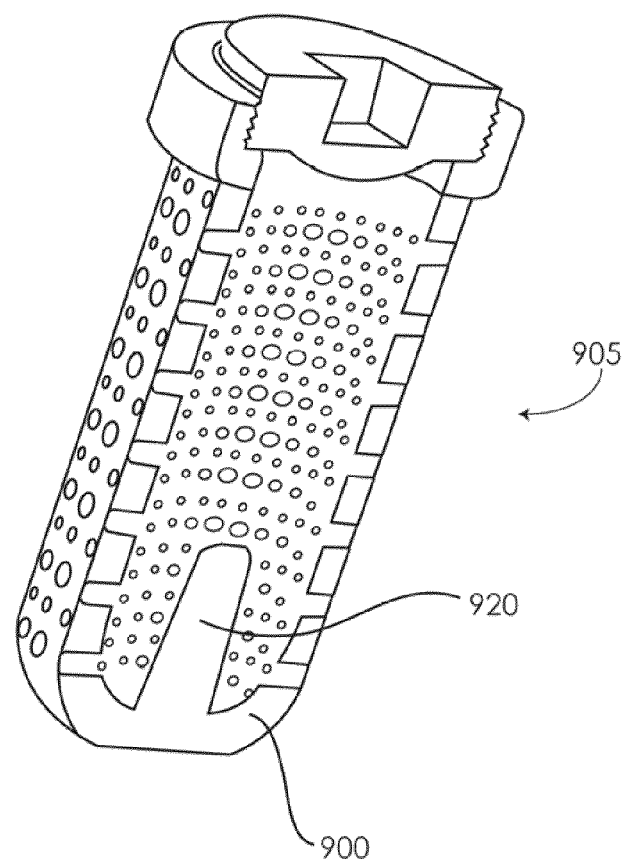
FIG. 34 shows an alternative embodiment of an assembled bone repair device with a porous body and with an internal pressure-amplifying feature.

FIG. 34 shows a cross sectional view of an alternate embodiment of the porous body portion 900' of an assembled repair device 905' that includes an internal tissue expander feature 920 disposed to induce radial extrusion of the bone core tissue through the orifices.

Figure 35:
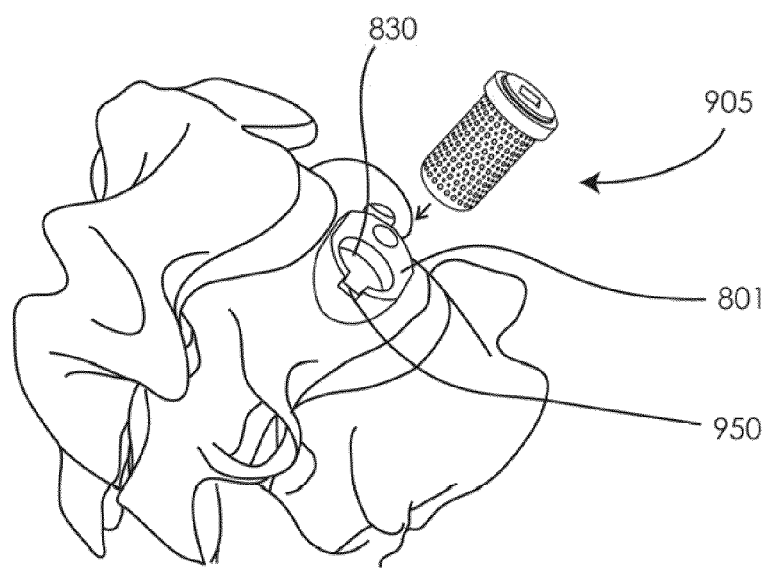
FIG. 35 shows a bone repair device with a porous body containing bone tissue poised in a position from where it is about to be implanted in an access channel within a vertebral body.
Figure 36:
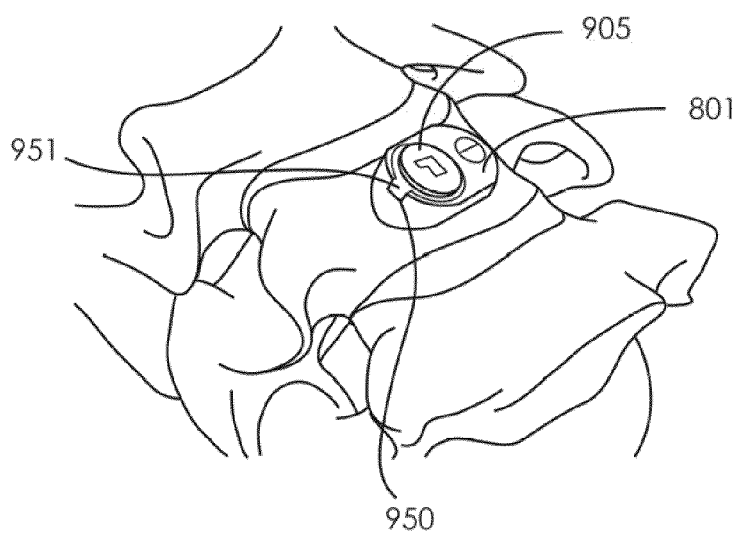
FIG. 36 shows the bone repair device of FIG. 35 implanted in the vertebral body, and locked into a bone plate.
Figure 37:
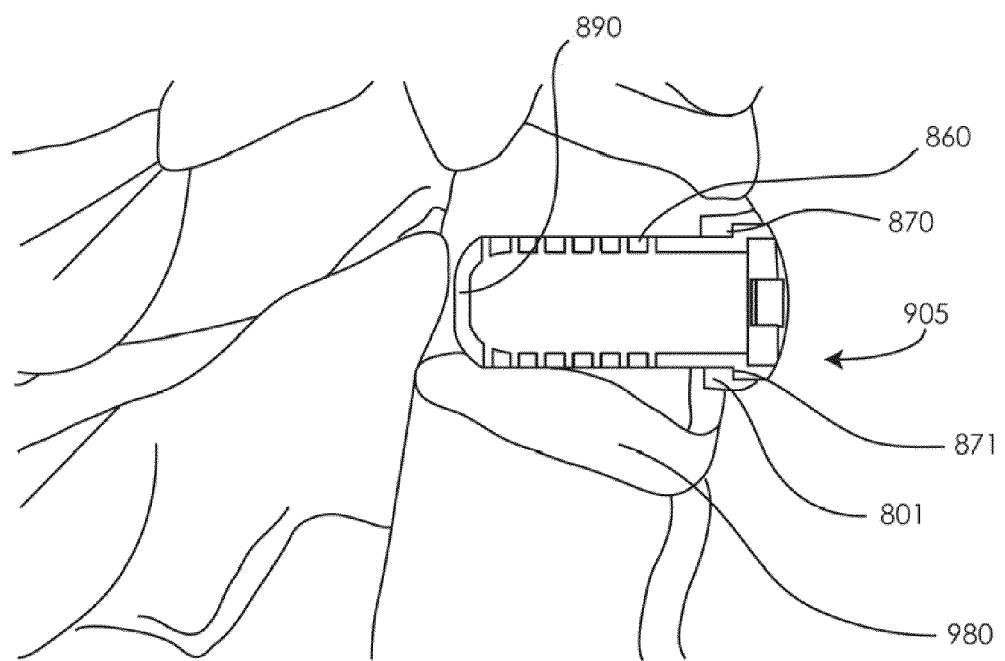
FIG. 37 shows a lateral cross sectional view of a bone repair device with a porous body containing bone tissue, in situ, within an access channel in a host vertebral body.

FIGS. 35 and 36 show similar views of the porous cage device embodiment 905 as were provided earlier by FIGS. 15 and 16 for solid bone repair device 500 embodiments. FIG. 37 shows a cross sectional view of the implanted device 905 within an intravertebral access channel 470. Upon completion of the surgical procedure through the access channel, the bone repair implant assembly 905 (containing the harvested bone graft core 860) is introduced into the transcorporal access channel through the aperture 830 in the implanted bone plate device 100. In one exemplary embodiment, the bone repair assembly 905 has an abutting surface disposed to cooperate with a mating surface of engagement 871 on the bone plate implant. The completed mating of the bone repair assembly 905 with the bone plate 100 prevents the distal tip 890 of the implant assembly from penetrating into the spinal cord volume posterior to the vertebral body.

The implantable repair device assembly 905 further has an orientation and locking feature 951 disposed to engage a mating feature 950 on the implantable bone plate 100 so as to control the radial orientation of the implant with respect to the bone plate and to lockably engage the bone repair implant device with the bone plate implant so as to prevent migration or expulsion of the bone repair implant assembly 905 out of the access channel. Such radial orientation of the implant relative to the access channel may be particularly advantageous when the bottom or distal end of the repair device body 900 is formed at an angle (not shown) to completely fill the access channel.

As a consequence of the implantation of the bone repair assembly 905 within the access channel, the general mechanical integrity of the vertebral body has been restored, the internal void of the access channel has been filled in a manner such that native disc material 980 cannot migrate into the channel, bone tissue (typically autologous) has been re-implanted in a manner that establishes intimate contact between the bone graft and the cancellous bone of the vertebra thereby promoting blood profusion and rapid bone healing.

What is claimed is:

1. A method for performing a procedure through a vertebral body overlaying a site in need of a medical procedure comprising:

attaching an integrated device comprising a bone plate portion and trajectory control sleeve portion on an anterior surface of the vertebral body;

inserting at least a portion of a bone cutting tool through the trajectory control sleeve;

forming an access channel through the vertebral body by removing bone with the bone cutting tool, the access channel following a prescribed trajectory from an anterior entry point to a prescribed opening on a posterior surface of the vertebral body in the locale of the site in need of the medical procedure;

disengaging the integrated device from the vertebral body; and performing the medical procedure through the access channel and the opening on the posterior surface of the vertebral body, wherein the bone plate portion of the attached integrated device comprises a curved surface configured to contact the anterior surface of the single vertebral body and is temporarily secured to the anterior surface of the vertebral body, wherein the trajectory control sleeve portion of the attached integrated device comprises a cylinder configured to receive at least a portion of the bone cutting tool, wherein only a single access channel with a prescribed trajectory from the anterior entry to a prescribed posterior opening adjacent a spinal cord is formed in the forming step, the anterior entry of the single access channel having a center that is generally at a mid-point on a cranio-caudal length of the vertebral body and generally offset from a medio-lateral mid-point of the vertebral body, the single access channel proceeding with a circular cross-section along a single, straight axis from the anterior entry in a posterior, caudal and lateral direction to the prescribed posterior opening, the prescribed posterior opening being located at or adjacent to the base of the posterior surface of the single vertebral body, the single access channel having an angle in the cranio-caudal direction of between about 1 degree and about 30 degrees from perpendicular to the anterior surface at the anterior entry, the single access channel having an angle in the medio-lateral direction of between about 1 degree and about 30 degrees from perpendicular to the anterior surface at the anterior entry, the single access channel having a diameter of between about 5 mm and about 8 mm, wherein the penetration of the cutting tool into the vertebral body is precisely limited to a prescribed depth in the forming step by a portion of the cutting tool contacting a portion of the attached integrated device.

2. The method of claim 1 wherein performing the medical procedure may include any of performing a medical observation, an exploratory procedure, a diagnostic procedure, a surgical procedure, or a therapeutic delivery procedure.

3. The method of claim 2 wherein performing the surgical procedure includes decompressing a neural element.

4. The method of claim 3 wherein decompressing a neural element may include decompressing any of an individual nerve root, a spinal cord, or a cauda equina.

5. The method of claim 1 wherein the site in need of a medical procedure may include a portion or the whole of a herniated disc, an osteophyte, a thickened ligament, a tumor, a hematoma, a degenerative cyst, or any other compressing pathology.

6. The method of claim 1 wherein the forming the access channel includes forming the channel with a constant, circular cross-section along a single, straight axis aligned with the trajectory control sleeve.

7. The method of claim 1 further comprising, following the medical procedure, repairing the access channel with an implantable bone repair device, the device having an external geometry complementary to the internal geometry of the channel.

8. The method of claim 7 wherein repairing the access channel includes in-growing bone from the vertebral body into at least a portion of the surface of the bone repair device.

9. The method of claim 7 wherein repairing the access channel includes stimulating bone growth within the bone repair device by providing an osteogenic agent within the repair device.

10. The method of claim 7 wherein repairing the access channel includes placing a portion of harvested bone tissue within a bone repair device that comprises a porous cage.

11. The method of claim 10 further comprising allowing intimate contact between the bone tissue within the bone repair device and bone tissue of the vertebral body.

12. The method of claim 10 further comprising perfusing at least some bone tissue or bone-associated biological fluid from the bone repair device into the vertebral body.

13. The method of claim 12 wherein the perfusing step comprises compressing bone tissue inside the porous cage.

14. The method of claim 13 wherein the compressing step is at least partially performed after the porous cage has been placed inside the access channel.

15. The method of claim 10 further comprising allowing the bone tissue within the bone repair device to heal together with the bone tissue of the vertebral body.

* * * * *